United States Patent
Gébleux et al.

(10) Patent No.: US 10,906,963 B2
(45) Date of Patent: Feb. 2, 2021

(54) NON-GLYCOSYLATED ANTI-TENASCIN ANTIBODY

(71) Applicant: Philogen S.P.A, Siena (IT)

(72) Inventors: Rémy Gébleux, Olten (CH); Sarah Wulhfard, Baden (CH)

(73) Assignee: Philogen S.P.A, Siena (IT)

( * ) Notice: Subject to any disclaimer, the term of this patent is extended or adjusted under 35 U.S.C. 154(b) by 203 days.

(21) Appl. No.: 16/093,357

(22) PCT Filed: Apr. 12, 2017

(86) PCT No.: PCT/EP2017/058885
§ 371 (c)(1),
(2) Date: Oct. 12, 2018

(87) PCT Pub. No.: WO2017/178569
PCT Pub. Date: Oct. 19, 2017

(65) Prior Publication Data
US 2019/0127451 A1 May 2, 2019

(30) Foreign Application Priority Data

Apr. 15, 2016 (GB) .................................. 1606653.2

(51) Int. Cl.
| | | |
|---|---|---|
| *C07K 16/18* | (2006.01) | |
| *A61K 47/68* | (2017.01) | |
| *A61K 45/06* | (2006.01) | |
| *A61P 35/00* | (2006.01) | |
| *C07K 14/55* | (2006.01) | |
| *A61K 39/00* | (2006.01) | |

(52) U.S. Cl.
CPC .............. *C07K 16/18* (2013.01); *A61K 45/06* (2013.01); *A61K 47/6803* (2017.08); *A61P 35/00* (2018.01); *C07K 14/55* (2013.01); *A61K 2039/505* (2013.01); *C07K 2317/41* (2013.01); *C07K 2317/56* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

| | | |
|---|---|---|
| WO | 2006050834 A2 | 5/2006 |
| WO | 2010078916 A1 | 7/2010 |

OTHER PUBLICATIONS

Brack et al (Clinical Cancer Research, 2006, 12:3200-3208).*
Spenle et al. (2015) Tenascin-C: Exploitation and collateral damage in cancer management: Cell Adhesion & Migration 9:1-2, 141-153.

* cited by examiner

*Primary Examiner* — Laura B Goddard
(74) *Attorney, Agent, or Firm* — Pamela J. Sherwood; Bozicevic, Field & Francis LLP

(57) ABSTRACT

The present invention relates to variants of the anti-tenascin antibody F16 which are modified to abolish N-glycosylation at positions 88 to 90 in the VL domain. This results in dramatically improved properties, such as improved binding affinity and tumour biodistribution in vivo. Variant F16 antibody molecules and methods for their production and use are provided.

21 Claims, 12 Drawing Sheets

Specification includes a Sequence Listing.

NON-GLYCOSYLATED ANTI-TENASCIN ANTIBODY

FIELD

The present invention relates to antibody molecules that bind human tenascin-C, and uses of such molecules in the treatment and diagnosis of diseases, such as cancer.

BACKGROUND

Asparagine (N)-linked glycosylation is an important post-translational modification that results in the covalent attachment of oligosaccharides onto asparagine residues in a protein sequence. The acceptor substance of N-glycosylation is an asparagine within the consensus sequence N-X-S/T, where X can be any amino acid except proline (Schwarz and Aebi, 2011 Curr Opin Struct Biol. 2011 21(5):576-82). However, the presence of the consensus sequence is not sufficient to conclude that an asparagine residue is N-glycosylated because the folding of the protein and the solvent accessibility of the consensus sequence also plays an important role in the regulation of N-glycosylation (Pless et al (1977) PNAS USA 74 134-138; Bause et al Biochem J, 209 (1983), pp. 331-336; Lam et al (2013) Genomics, Proteomics Bioinformatics 11 2 96-104).

In immunoglobulin G (IgG), the Asp297 located in the Fc region of the heavy chain is glycosylated. The sugar core anchored to this glycosylation site plays a critical role in IgG effector functions and, accordingly, has been and is extensively studied. N-glycosylation can also be found in variable domains of heavy and light chains of a small number of IgGs. Much less is known about the function of glycosylation sites within the variable domain. Not all glycosylation sites within antibody variable domains are actually glycosylated (Wright et al EMBO J. 1991 October; 10(10): 2717-2723). Furthermore, various different studies have found that removing the N-glycosylation from the variable region can result in decreased antigen binding affinity (Leibiger et al. Biochem J. 1999; 338:529-38, Wright et al EMBO J. 1991 October; 10(10): 2717-2723; Jacquemin Haemophilia (2010) 16 (102) 16-19; Khurana et al Biochem Biophys Res Commun (1997) 234 (2) 465-469; Coloma J Immunol (1999) 162(4) 2162-2170) or have no apparent effect (Sato et al., Hum Antibodies Hybridomas. 1996; 7(4):175-83). N-glycosylation of antibody variable regions has also been reported to reduce aggregation (Wu et al (2010) PEDS 23 8 643-651).

The anti-tenascin C antibody F16 (Brack et al. Clin Cancer Res. 2006 May 15; 12(10):3200-8.) binds to the extradomain A1 of tenascin-C. This domain is virtually undetectable in normal adult tissues but is strongly expressed at sites of physiological angiogenesis and tumour angiogenesis (Brack et al., 2006 supra). The F16 antibody has efficacy in vivo and has been successfully employed for the development of armed antibodies, in particular immunocytokines. The F16 antibody has begun clinical testing in oncology (Pasche and Neri, 2012 Drug Discov Today. 17(11-12):583-90). There have been no reports of N-glycosylation within the variable domains of the F16 antibody.

SUMMARY

The present invention relates to the unexpected finding that the light chain variable (VL) domain of the anti-tenascin antibody F16 is N-glycosylated and furthermore the modification of the F16 antibody to abolish this N-glycosylation results in dramatically improved properties, such as improved binding affinity and tumour biodistribution in vivo.

An aspect of the invention provides an antibody molecule that binds human tenascin-C comprising:
(a) a heavy chain variable (VH) domain comprising the amino acid sequence of SEQ ID NO: 1 or an amino acid sequence having 5 or fewer sequence alterations relative to SEQ ID NO: 1; and
(b) a light chain variable (VL) domain comprising the amino acid sequence of SEQ ID NO: 2 or an amino acid sequence having 5 or fewer sequence alterations relative to SEQ ID NO: 2, said alterations being at positions other than 88 and 90.

Preferably, the residue at position 88 of the VL domain is not Asparagine, and may be, for example, Glutamine or Alanine. Most preferably, the residue at position 88 is Glutamine. The residue at position 90 of the VL domain is preferably Serine or Threonine. Most preferably, the residue at position 90 is Serine.

A preferred antibody molecule that binds human tenascin-C may comprise:
(a) a heavy chain variable (VH) domain comprising the amino acid sequence of SEQ ID NO: 1; and
(b) a light chain variable (VL) domain comprising the amino acid sequence of SEQ ID NO: 3.

Another aspect of the invention provides an antibody molecule that binds human tenascin-C comprising:
(a) a heavy chain comprising the amino acid sequence of SEQ ID NO: 5, or an amino acid sequence having 5 or fewer sequence alterations relative to SEQ ID NO: 5; and
(b) a light chain comprising the amino acid sequence of SEQ ID NO: 6 or an amino acid sequence having 5 or fewer sequence alterations relative to SEQ ID NO: 6, said alterations being at positions other than 88 and 90.

Another aspect of the invention provides an antibody molecule that binds human tenascin-C as described above conjugated to a cytokine, preferably IL-2.

Another aspect of the invention provides an isolated nucleic acid encoding an antibody molecule described above; the VL domain of an antibody molecule described above or the light chain of an antibody molecule described above.

Another aspect of the invention provides a method of treating a proliferative disorder, such as cancer, comprising administering an antibody molecule described herein to an individual in need thereof.

Another aspect of the invention provides a method of diagnosing a proliferative disorder, such as cancer, in an individual, wherein the method comprises administering the antibody molecule to the individual and detecting binding of the antibody molecule in the individual.

Other aspects of invention provide an antibody molecule described herein for use in a method of treating or diagnosing a proliferative disorder, such as cancer, and the use of an antibody molecule described herein in the manufacture of a medicament for use in a method of treating or diagnosing a proliferative disorder, such as cancer.

BRIEF DESCRIPTION OF FIGURES

FIG. 1A shows the results of an SDS-PAGE analysis of the non-reduced (lane 1) and reduced (lane 2) antibody. FIG. 1B shows the results of size exclusion chromatography (SEC)

of the mutant antibody. FIG. 1C is a deconvoluted MS-spectrum. The major peak at 22704 Da corresponds to the Light Chain (expected mass 22707 Da), while peaks around 50500 Da correspond to the glycosylated Heavy Chain.

DETAILED DESCRIPTION

Figure 1A:
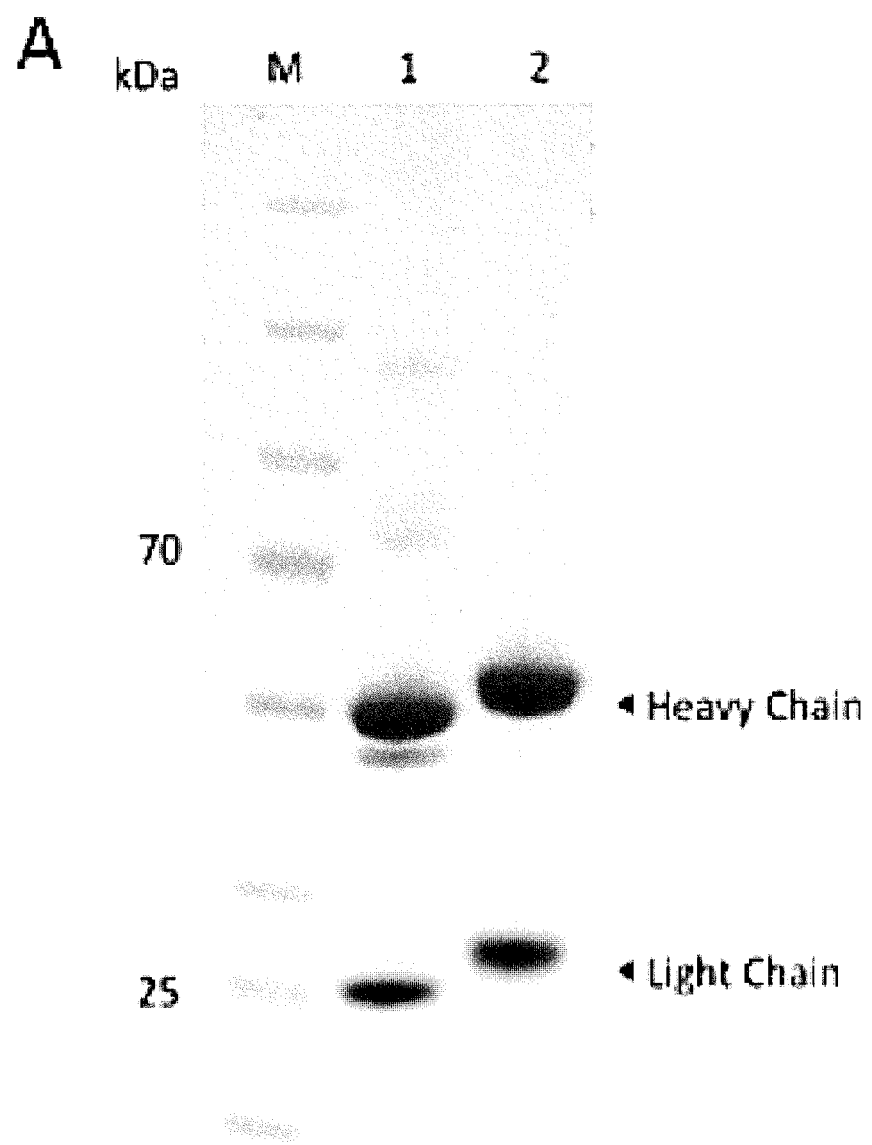
FIGS. 1A, 1B and 1C show the results of experiments characterising the mutant IgG(F16)-3S-N88Q antibody.

Tenascin-C(Gene ID: 3371; NP_002151.2 GI: 153946395) is a large hexameric glycoprotein of the extracellular matrix which modulates cellular adhesion. It is involved in processes such as cell proliferation and cell migration and is associated with changes in tissue architecture as occurring during morphogenesis and embryogenesis as well as under tumorigenesis or angiogenesis. Several isoforms of tenascin-C can be generated as a result of alternative splicing which may lead to the inclusion of (multiple) domains in the central part of this protein, ranging from domain A1 to domain D (Borsi L et al Int J Cancer 1992; 52:688-692, Carnemolla B et al. Eur J Biochem 1992; 205:561-567).

The F16 antibody binds to the A1 domain of human tenascin-C and has been widely described in the art (Schliemann et al. (2015) Cancer Immunol. Res., 3, 547-556; Catania et al. (2015) Cell Migr. Adhes., 9: 1-2, 14-21; Gutbrodt et al. (2013) Sci. Trans. Med., 5, 201ra118; Heuveling et al. (2013) J Nucl. Med., 54, 397-401; De Braud et al. (2011) J Clin. Oncol. 29, 2595; De Braud et al. (2010) J Clin. Oncol., 28, e13017; Pedretti et al. (2010) Br J Cancer, 103, 827-836; Marlind et al. (2008) Clin. Cancer Res 14, 6515-24; Brack et al. (2006) Clin. Cancer Res., 12, 3200-3208; WO2006/050834). Frey et al. (2011) Exp. Dermatol, 20, 685-688; Schwager et al., Head Neck Oncol (2011) 3:25; Pedretti et al. (2010) Atherosclerosis (2010) 208, 382.389; Schliemann et al. (2009) Leuk Res., 33, 1718-1722; Pedretti et al., (2009) 64, 28-33. The F16 antibody may comprise the VH and VL domains of SEQ ID NOs: 1 and 7, respectively, for example the heavy and light chains of SEQ ID NOs: 4 and 5, respectively.

This invention relates to a modified F16 anti-tenascin antibody molecule which lacks N-glycosylation sites within the VL domain. In particular, the modified F16 antibody lacks the N-glycosylation site at positions 88-90 of the VL domain that is present in the parent F16 antibody. The modified F16 antibody displays improved properties over the parent F16 antibody, such as improved binding affinity, reduced aggregation and improved tumour in vivo biodistribution.

A modified F16 antibody molecule as described herein may comprise:

(a) a heavy chain variable (VH) domain comprising the amino acid sequence of SEQ ID NO: 1 or an amino acid sequence having 5 or fewer sequence alterations relative to SEQ ID NO: 1; and (b) a light chain variable (VL) domain comprising the amino acid sequence of SEQ ID NO: 2 or an amino acid sequence having 5 or fewer sequence alterations relative to SEQ ID NO: 2, said alterations being at positions other than 88 and 90.

The modified F16 antibody molecule specifically binds to the A1 domain of human tenascin-C i.e. it displays the same binding specificity as the parent F16 antibody.

The VL domain of the modified F16 antibody molecule lacks the N-glycosylation signal at residues 88-90 that is present in the parent F16 antibody molecule. For example, the residues at positions 88 and 90 of the VL domain of the modified F16 antibody molecule are not (i) Asn and Ser, (ii) Asn and Thr, or (iii) Asn and Cys, respectively. Preferably, the VL domain of the modified F16 antibody molecule comprises a sequence alteration at one or both of positions 88 and 90, most preferably position 88 relative to the parent F16 antibody (i.e. the N-glycosylation signal is removed by a single amino substitution at position 88).

In addition to the removal of the N-glycosylation signal of residues 88-90, the VL domain of the modified F16 antibody molecule may comprise less than other 5 sequence alterations relative to the VL domain of the parent F16 antibody. Preferably, the five or fewer sequence alterations are outside the VL CDRs of the antibody. For example, the modified F16 may contain the same VL CDR sequences as the parent F16 antibody. Preferably, other than sequence alterations at one or more of positions 88 to 90, the modified F16 antibody molecule (SEQ ID NO: 2) comprises the same VL domain as the parent F16 antibody molecule (SEQ ID NO: 7).

The VH domain of the modified F16 antibody molecule may comprise less than 5 sequence alterations relative to the VH domain of the parent F16 antibody. Preferably, the five or fewer sequence alterations are outside the VH CDRs of the antibody. For example, the modified F16 may contain the same VH CDR sequences as the parent F16 antibody. Preferably, the modified F16 antibody molecule comprises the same VH domain as the parent F16 antibody molecule (SEQ ID NO: 1).

Sequence alterations may include single amino acid substitutions, deletions or insertions. The substitutions may be conservative substitutions. For example, the antibody molecule may comprise a VH domain having the amino acid sequence of SEQ ID NO: 1 with 1, 2, 3 or 4 single amino acid substitutions, deletions or insertions. The amino acid sequence of the VH domain of a modified F16 antibody molecule may have 90% or higher, 95% or higher or 98% or higher sequence identify to SEQ ID NO: 1, The antibody molecule may comprise a VL domain having the amino acid sequence of SEQ ID NO: 2 with 1, 2, 3 or 4 single amino acid substitutions, deletions or insertions at positions other than 88 to 90. The amino acid sequence of the VL domain of a modified F16 antibody molecule may have 90% or higher, 95% or higher or 98% or higher sequence identify to SEQ ID NO: 2, SEQ ID NO: 3 or SEQ ID NO: 7. Preferably, the sequence alterations are outside the CDRs of the antibody molecule.

Techniques for the introduction of substitutions, deletions or insertions within the amino acid sequences of antibody VH or VL domains are widely available in the art. Antibodies may be generated with sequence substitutions, deletions or insertions that may or may not be predicted to have a minimal or beneficial effect on activity, and tested for ability to bind to the A1 domain of human tenascin-C and/or for any other desired property.

In some embodiments, the VH domain of the modified F16 antibody molecule may comprise an Ala instead of Met at position 4 of VHCDR1 (position 34 of SEQ ID NO: 1).

In some embodiments, Cys residues in the modified F16 antibody may be replaced by Ser residues. For example, the modified F16 antibody may comprise Ser instead of Cys at one or more, for example 1, 2 or 3, positions in the heavy chain or light chains (Gebleux et al Mol Cancer Ther. (2015) 14(11):2606-12). Preferred modified F16 antibody molecules may comprise a single Cys residue located at the N or C terminal of the antibody molecule. This may be useful for the conjugation of bioactive molecules, such as cytotoxic drugs, to the modified F16 antibody.

In preferred embodiments, the amino acid sequences of the VH and VL domains of the modified F16 antibody molecule are identical to the parent F16 antibody other than at one or both positions 88 and 90 in the VL domain. For example, a modified F16 antibody molecule may comprise:
 (a) a heavy chain variable (VH) domain comprising the amino acid sequence of SEQ ID NO: 1; and
 (b) a light chain variable (VL) domain comprising the amino acid sequence of SEQ ID NO: 2.

Preferably, the residue at position 88 of the VL domain is not Asparagine. For example, the residue at position 88 of the VL domain may be Glutamine or Alanine. In some embodiments, the residue at position 88 of the VL domain is Glutamine or Alanine, preferably Glutamine and the residue at position 90 of the VL domain is Serine. A preferred antibody molecule may comprise:
 (a) a heavy chain variable (VH) domain comprising the amino acid sequence of SEQ ID NO: 1; and
 (b) a light chain variable (VL) domain comprising the amino acid sequence of SEQ ID NO: 3.

In another aspect, an antibody molecule that binds human tenascin-C may comprise:
 (a) a heavy chain having an amino acid sequence of SEQ ID NO: 5, or an amino acid sequence having less than 5 sequence alterations relative to SEQ ID NO: 5; and
 (b) a light chain having an amino acid sequence of SEQ ID NO: 6 or an amino acid sequence having less than 5 sequence alterations relative to SEQ ID NO: 6, said alterations being at positions other than one or more of 88 to 90.

In some embodiments, the antibody molecule may comprise the VH and VL domains of SEQ ID NOs: 1 and 3, respectively. For example, a preferred antibody molecule may comprise:
 (a) a heavy chain having an amino acid sequence of SEQ ID NO: 5; and
 (b) a light chain having an amino acid sequence of SEQ ID NO: 6.

In some embodiments, an antibody molecules described above may comprise one or more Cys residues, preferably N or C terminal Cys residues. Cys residues may be useful in coupling bioactive molecules, such as cytotoxic compounds, to the antibody molecule.

Modified F16 antibody molecules as described herein are human monoclonal antibody molecules.

Modified F16 antibody molecules include immunoglobulins and fragments thereof, and may be partly or wholly synthetically produced, for example as recombinant molecule.

A modified F16 antibody molecule may be in any format and may include any polypeptide or protein comprising an immunoglobulin antigen-binding site comprising paired VH and VL domains, including Fab, Fab', Fab'-SH, $Fab_2$, $Fab_3$, diabodies, triabodies, tetrabodies, minibodies, scFvs and, small immunoproteins (SIPs), as well as whole antibodies of any isotype or sub-class, and antibody fragments. Antibody molecules and methods for their construction and use are described, in for example Holliger & Hudson, Nature Biotechnology 23(9):1126-1136 (2005).

In some preferred embodiments, the modified F16 antibody molecule is an scFv, diabody or small immunoprotein (SIP).

A small immune protein (SIP) may comprise an scFv molecule comprising the VH and VL domains of a modified F16 antibody molecule described herein fused to the $CH_4$ domain of human immunoglobulin E.

In other preferred embodiments, the modified F16 antibody molecule may be a whole antibody. For example, the modified F16 antibody molecule may be an IgG, IgA, IgE or IgM or any of the isotype sub-classes, particularly IgG1 and IgG4.

A modified F16 antibody molecule may bind human tenascin C with a $K_D$ of 1 µM or less, 100 nM or less, 50 nM or less, 25 nM or less, 10 nM or less or 1 nM or less, preferably 10 nM or less.

Suitable techniques for the measurement of affinity are well-known in the art (see for example Brack et al. (2006)) and include surface plasmon resonance, for example using the BIAcore3000 system under standard conditions. Surface plasmon resonance involves passing an analyte in fluid phase over a ligand attached to a support, and determining binding between analyte and ligand. Surface plasmon resonance may for example be performed by passing an antibody molecule in fluid phase over A1 domain of tenascin-C immobilised on a solid support. An affinity constant $K_D$ may be calculated from the ratio of rate constants kd1/ka1 as determined by surface plasmon resonance.

Preferably, a modified F16 antibody molecule binds human tenascin C with a higher affinity than the parent F16 antibody molecule, for example when measured using surface plasmon resonance, e.g. using a BIAcore3000 instrument. For example, the modified F16 antibody molecule may bind human tenascin C with 2 fold or more, 4 fold or more, 6 fold or more or 8 fold or more higher affinity than the parent F16 antibody molecule, The parent F16 antibody molecule may comprise the F16 VH domain of SEQ ID NO: 1 and the F16 VL domain of SEQ ID NO: 7.

Other aspects of the invention provide an isolated nucleic acid molecule encoding a modified F16 antibody molecule as described above or a light chain or VL domain thereof, and a vector comprising such a nucleic acid.

Nucleic acid molecules may comprise DNA and/or RNA and may be partially or wholly synthetic. Reference to a nucleotide sequence as set out herein encompasses a DNA molecule with the specified sequence, and encompasses a RNA molecule with the specified sequence in which U is substituted for T, unless context requires otherwise.

Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in mammalian cells. A vector may also comprise sequences, such as origins of replication, promoter regions and selectable markers, which allow for its selection, expression and replication in bacterial hosts such as *E. coli.*

Vectors may be plasmids, viral e.g. phage, or phagemid, as appropriate. For further details see, for example, Molecular Cloning: a Laboratory Manual: 3rd edition, Russell et al., 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, are described in detail in Current Protocols in Molecular Biology, Ausubel et al. eds. John Wiley & Sons, 1992.

A nucleic acid or vector as described herein may be introduced into a host cell. Techniques for the introduction of nucleic acid into cells are well-established in the art and any suitable technique may be employed, in accordance with the particular circumstances. For eukaryotic cells, suitable techniques may include calcium phosphate transfection, DEAE-Dextran, electroporation, liposome-mediated transfection and transduction using retrovirus or other virus, e.g. adenovirus, AAV, lentivirus or vaccinia. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well-known in the art.

The introduced nucleic acid may be on an extra-chromosomal vector within the cell or the nucleic acid may be integrated into the genome of the host cell. Integration may be promoted by inclusion of sequences within the nucleic acid or vector which promote recombination with the genome, in accordance with standard techniques.

The introduction of the nucleic acid may be followed by expression of the nucleic acid in the cells to produce the encoded modified F16 antibody molecule. Host cells (which may include cells actually transformed although more likely the cells will be descendants of the transformed cells) may be cultured in vitro under conditions for expression of the nucleic acid, so that the encoded modified F16 antibody molecule is produced. When an inducible promoter is used, expression may require the activation of the inducible promoter.

Another aspect of the invention provides a recombinant cell comprising a nucleic acid or vector that expresses a modified F16 antibody molecule as described above.

An aspect of the invention provides a method of producing a modified F16 antibody molecule comprising expressing a nucleic acid encoding a modified F16 antibody molecule in a host cell and optionally isolating and/or purifying the modified F16 antibody molecule thus produced.

A range of host cells suitable for the production of recombinant modified F16 antibody molecules are known in the art. Suitable host cells may include eukaryotic cells, including mammalian cells such as CHO and CHO-derived cell lines (Lec cells), HeLa, COS, HEK293 and HEK-EBNA cells, amphibian cells such as *Xenopus* oocytes, insect cells such as *Trichoplusia ni*, Sf9 and Sf21 and yeast cells, such as *Pichia pastoris.*

Suitable techniques for the recombinant production of antibody molecules are well-known in the art (see for example, Harlow and Lane, Antibodies: A Laboratory Manual, Cold Spring Harbor; Chadd et al. (2001), Current Opinion in Biotechnology 12: 188-194); Andersen et al. (2002) Current Opinion in Biotechnology 13: 117; Larrick & Thomas (2001) Current Opinion in Biotechnology 12:411-418.). Preferably, a modified F16 antibody molecule produced by expression in mammalian cells.

Following expression, the modified F16 antibody molecule may be isolated and/or purified. Suitable techniques for the isolation and/or purification of recombinant polypeptides are well-known in the art and include, for example HPLC, FPLC or affinity chromatography.

Where appropriate, antibody molecules may be purified on an affinity column comprising immobilised antigen. Alternatively, antibody molecules may be purified on an affinity column comprising immobilised protein A and/or G, optionally followed by ion-exchange chromatography aimed at eliminating the residual protein contaminants as well as the DNA and the LPS and/or exclusion chromatography on Sepharose gel in order to eliminate aggregates, such as dimers or other multimers.

After production, a modified F16 antibody molecule may be investigated further, for example to determine its pharmacological or other properties and/or activity. Suitable techniques of protein analysis are well-known in the art.

Modified F16 antibody molecules may be further modified by chemical modification, for example by PEGylation, or by incorporation in a liposome, to improve their pharmaceutical properties, for example by increasing in vivo half-life. For example, a modified F16 antibody molecule may be attached to one or more polyethylene glycol (PEG) or other moieties (Cantin et al. 2002, Am. J. Respir. Cell Mol. Biol. 27; 659-665). A modified F16 antibody molecule may be mono-pegylated or poly-pegylated (for example, with 2-6 PEG moieties). Suitable pegylation methods are well known in the art.

In some embodiments, a modified F16 antibody molecule may be conjugated to a bioactive molecule.

Suitable bioactive molecules include cytokines. The VH domain or VL domain of the modified F16 antibody molecule may be fused to the cytokine to form an immunoconjugate or immunocytokine. The cytokine moiety may be fused upstream (N-terminal) or downstream (C-terminal) of the antibody molecule. Typically the antibody molecule, or component thereof, and cytokine are joined via a peptide linker, e.g. a peptide of about 5-25 residues, e.g. 10-20 residues, preferably about 15 residues. Suitable cytokines include IL-2, IL-4, IL-12, IL-15 and TNFα. Preferably, the cytokines are human cytokines.

In some preferred embodiments, the modified F16 antibody molecule may be conjugated to IL2 to form an antibody-cytokine immunoconjugate. Interleukin-2 (IL2) is a secreted cytokine which is involved in immunoregulation and the proliferation of T and B lymphocytes. IL2 has been shown to have a cytotoxic effect on tumour cells and recombinant human IL2 (aldesleukin: Proleukin™) has FDA approval for treatment of metastatic renal carcinoma and metastatic melanoma. The sequence of human IL2 is publicly available under sequence database reference NP_000577.2 GI: 28178861 and shown in SEQ ID NO: 12.

Suitable bioactive molecules include cytotoxic agents, such as monomethyl auristatin E (MMAE), dolastatins, vinblastines, photosensitisers, toxin polypeptides, such as *Pseudomonas* exotoxin, ricin α-chain and angiogenin, toxic small molecules, such as maytansine, calicheamicin, epothilone, tubulysin, duocarmycins, anthracyclines, pirrolobenzodiazepines, indolinobenzodiazepines and, amatoxins and other drugs, chemokines, pro-coagulant factors (e.g. tissue factor) and enzymes.

Suitable detectable labels include radioisotopes such as iodine-125, iodine-131, yttrium-90, indium-111 and technetium-99; fluorochromes, such as fluorescein, rhodamine, phycoerythrin, Texas Red and cyanine dye derivatives for example, Cy7 and Alexa750; chromogenic dyes, such as diaminobenzidine; latex beads; enzyme labels such as horseradish peroxidase; phosphor or laser dyes with spectrally isolated absorption or emission characteristics; and chemical moieties, such as biotin, which may be detected via binding to a specific cognate detectable moiety, e.g. labelled avidin.

Bioactive molecules may include therapeutic radioisotopes. Suitable therapeutic radioisotopes include $^{131}$I, $^{90}$Y, $^{124}$I, $^{211}$At, $^{77}$Br, and $^{76}$Br.

The modified F16 antibody molecule may be conjugated to the bioactive molecule by any suitable covalent or non-covalent linkage. Preferably, the modified F16 antibody molecule is conjugated to the bioactive molecule by a covalent linker, such as a disulphide or peptide. For example, a bioactive molecule may be conjugated via a disulphide linkage to a Cys residue in the modified F16 antibody molecule.

In some embodiments, the bioactive molecule may be conjugated to the antibody molecule by a cleavable linker. The linker may allow release of the bioactive molecule from the antibody molecule at a site of therapy. Linkers may include amide bonds (e.g. peptidic linkers), disulphide bonds or hydrazones. Peptide linkers for example may be cleaved by site specific proteases, disulphide bonds may be cleaved by the reducing environment of the cytosol and hydrazones may be cleaved by acid-mediated hydrolysis.

Modified F16 antibody molecules, including conjugated antibody molecules, will usually be administered in the form of a pharmaceutical composition, which may comprise at least one component in addition to the antibody molecule. Thus, pharmaceutical compositions described herein may comprise, in addition to active ingredient, a pharmaceutically acceptable excipient, carrier, buffer, stabilizer or other materials well known to those skilled in the art. A method may comprise formulating a modified F16 antibody molecule with a pharmaceutically acceptable excipient. The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. The precise nature of the carrier or other material will depend on the route of administration, which may be by bolus, infusion, injection, intravenous or subcutaneous, or any other suitable route, as discussed below.

Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For parenteral, for example sub-cutaneous or intra-venous administration, e.g. by injection, the pharmaceutical composition comprising the modified F16 antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG). Suitable carriers, excipients, etc. can be found in standard pharmaceutical texts, for example, Remington's Pharmaceutical Sciences, 18th edition, Mack Publishing Company, Easton, Pa., 1990.

In some embodiments, the modified F16 antibody molecule may be provided in a lyophilised form for reconstitution prior to administration. For example, lyophilised antibody molecules may be re-constituted in sterile water and mixed with saline prior to administration to an individual.

Modified F16 antibody molecules as described herein may be used in a method of treatment of the human or animal body, including therapeutic and prophylactic or preventative treatment (e.g. treatment before the onset of a condition in an individual to reduce the risk of the condition occurring in the individual; delay its onset; or reduce its severity after onset).

A method of treating an individual may comprise administering a modified F16 antibody molecule described herein or a pharmaceutical composition comprising a modified F16 antibody molecule to an individual in need thereof.

An individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

In some preferred embodiments, the individual is a human. In other preferred embodiments, non-human mammals, especially mammals that are conventionally used as models for demonstrating therapeutic efficacy in humans (e.g. murine, primate, porcine, canine, or rabbit animals) may be employed.

Administration may be in a "therapeutically effective amount", this being sufficient to show benefit to a patient. Such benefit may be at least amelioration of at least one symptom. Thus "treatment" of a specified disease refers to amelioration of at least one symptom. The actual amount administered, and rate and time-course of administration, will depend on the nature and severity of what is being treated, the particular patient being treated, the clinical condition of the individual patient, the cause of the disorder, the site of delivery of the composition, the type of antibody molecule, the method of administration, the scheduling of administration and other factors known to medical practitioners.

Prescription of treatment, e.g. decisions on dosage etc., is within the responsibility of general practitioners and other medical doctors, and may depend on the severity of the symptoms and/or progression of a disease being treated. Appropriate doses of antibody are well known in the art (Ledermann et al. (1991) Int. J. Cancer 47: 659-664; and Bagshawe et al. (1991) Antibody, Immunoconjugates and Radiopharmaceuticals 4: 915-922). Specific dosages indicated herein, or in the Physician's Desk Reference (2003) as appropriate for the type of medicament being administered, may be used. A therapeutically effective amount or suitable dose of an antibody molecule for use in the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody molecule.

A typical antibody dose will be in the range 100 µg to 1 g for systemic applications. An initial higher loading dose, followed by one or more lower doses, may be administered. This is a dose for a single treatment of an adult patient, which may be proportionally adjusted for children and infants, and also adjusted according to antibody format in proportion to molecular weight. Treatments may be repeated at daily, twice-weekly, weekly or monthly intervals, at the discretion of the physician. Treatments may be every two to four weeks for subcutaneous administration and every four to eight weeks for intravenous administration. In some embodiments of the present invention, treatment is periodic, and the period between administrations is about two weeks or more, e.g. about three weeks or more, about four weeks or more, or about once a month. The treatment schedule for an individual may be dependent on the pharmocokinetic and pharmacodynamic properties of the antibody molecule, the route of administration and the nature of the condition being treated.

Treatment may be periodic, and the period between administrations may be about one week or more, e.g. about two weeks or more, about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of trauma, surgical treatment or invasive procedure. Suitable formulations and routes of administration are described above.

An individual suitable for treatment with a modified F16 antibody molecule may have a proliferative disorder.

Proliferative disorders are caused or characterized by increased cell growth and proliferation and may include a pre-malignant or malignant neoplasm or tumour, (e.g. histocytoma, glioma, astrocyoma, osteoma), cancer (e.g., lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, merkel cell carcinoma, pancreas cancer, brain cancer such as glioma, sarcoma, osteosarcoma, Kaposi's sarcoma, melanoma), a disease characterized by neovasculature or an angiogenic disease. Non-cancerous tumours of any of these tissues may also be treated. Cancers may be familial or sporadic.

Treatment of a tumour or cancer in an individual may comprise eradication of the tumour. However, for many forms of tumours, especially malignant cancers and aggressive forms such as glioblastoma, complete cure may not be possible. Treatment may comprise retarding tumour growth and/or reducing tumour volume. Treatment may comprise lengthening the overall survival or progression free survival of the individual. Treatment may comprise improving quality of life of the individual, e.g. by reducing one or more symptoms caused by the tumour. Treatment may comprise inhibiting regrowth of the tumour following tumour regression. Treatment according to the present invention may be used to achieve any or all of these therapeutic effects.

Proliferative disorders may also include diseases characterized by bone marrow neovasculature, such as leukaemia (e.g. CML, AML, HCL, CLL, or ALL, preferably AML) myelodysplastic syndromes, or multiple myeloma.

A pre-malignant or malignant condition may occur in any cell-type, including but not limited to, lung, colon, breast, ovarian, prostate, liver, pancreas, brain, and skin.

In some embodiments, a proliferative disorder suitable for treatment as described herein may be characterised by the presence of cells or tissue expressing a tenascin-C large isoform comprising the A1 domain, or in which expression of such an isoform is increased above normal levels i.e. aberrant expression of the tenascin-C large isoform.

Aspects of the invention provide a modified F16 antibody molecule as described herein for use in a method of treatment of a proliferative disorder; the use of a modified F16 antibody molecule as described herein in the manufacture of a medicament for the treatment of a proliferative disorder; and a method of treatment of a proliferative disorder comprising administering a modified F16 antibody molecule as described herein to an individual in need thereof.

Aspects of the invention provide a modified F16 antibody molecule as described herein for use in a method for inhibiting angiogenesis; the use of a modified F16 antibody molecule as described herein in the manufacture of a medicament for the inhibition of angiogenesis; and a method of inhibiting angiogenesis comprising administering a modified F16 antibody molecule as described herein to an individual in need thereof.

The modified F16 antibody molecule may be administered alone or in combination with other treatments, concurrently or sequentially or as a combined preparation with another therapeutic agent or agents, for the treatment of a disease, including a proliferative disorder, such as cancer. For example, a modified F16 antibody molecule may be used in combination with an existing therapeutic agent for the treatment of a proliferative disorder, such as cancer. Combined administration can include co-administration, either in a single pharmaceutical formulation or using separate formulations, or consecutive administration in either order but generally within a time period such that all active agents can exert their biological activities simultaneously.

Therapeutic agents may include anti-cancer compounds such as: alkylating agents, anti-metabolites, plant alkaloids and terpenoids, topoisomerase inhibitors, antitumour antibiotics, monoclonal antibodies, and corticosteroids. Examples of alkylating agents include cyclophosphamide, cisplatin, chlorambucil, carboplatin, and oxaliplatin. Examples of anti-metabolites include methotrexate, purine analogues such as cladribine, fludarabine, tioguanine and pentostatin, and pyrimidine analogues such as cytarabine, 5-fluorouracil, and floxuridine. Examples of plant alkaloids and terpenoids include vinca alkaloids, such as vincristine, vinblastine, vinorelbine, and vindesine; chemotherapeutic agents derived from podophyllotoxin such as etoposide phosphate and teniposide taxanes; and taxanes, which include paclitaxel and docetaxel. Examples of topoisomerase inhibitors include type I topoisomerase inhibitors such as camptothecins and type II topoisomerase inhibitors such as amsacrine, etoposide, etoposide phosphate, and teniposide. Examples of antitumour antibiotics include anthracyclines, such as doxorubicin and epirubicin, actinomycins, and bleomycin. Examples of monoclonal antibodies include rituximab, and examples of corticosteroids include prednisone and prednisolone.

Preferred anti-cancer compounds include: anthracyclines, cytarabine, vincristine, L-asparaginase, cyclophosphamide, fibromun, dacarbazine, methotrexate and 6-mercaptopurine, chlorambucil, cyclophosphamide, corticosteroids, such as prednisone and prednisolone, imatinib, cladribine, pentostatin, rituximab, chlorambucil, taxanes, such as paclitaxel, imidazotetrazinems, such as temozolomide; doxorubicin and immune checkpoint blockers, such as ipilimumab, pembrolizumab and nivolumab.

A modified F16 antibody molecule may be administered to an individual in need thereof in combination with chemotherapy or IgG-based immunotherapy. For example, anti-CD33 antibodies are currently being investigated for the treatment of AML in Phase IIb clinical trials. Suitable anti-CD33 antibodies are described, for example in Feldman et al. (2003) Leukemia. 2003 February; 17(2):314-8, Feldman et al. (2005) J Clin Oncol. 2005 Jun. 20; 23(18):4110-6. and Kobayashi et al. (2009) Int J Hematol. 89(4):460-9. In addition, IgG based anti-CD123 antibodies are also being investigated in the treatment of AML (Jin et al., 2009 Cell Stem Cell. 2; 5(1):31-42). Thus, in one example, IgG-based immunotherapy may involve treatment with an anti-CD33 or anti-CD123 antibody. Suitable anti-CD33 antibodies include lintuzumab.

Modified F16 antibody molecules as described herein may also be used in a method of diagnosis of the human or animal body. For example, a modified F16 antibody molecule may be used in patients suffering from a proliferative disorder, such as a disease characterized by neovasculature, for the detection or diagnosis of said disease.

A method may comprise causing or allowing binding of a modified F16 antibody molecule to domain A1 of tenascin-C. As noted, such binding may take place in vivo, e.g. following administration of a modified F16 antibody molecule, or in vitro.

The amount of binding of modified F16 antibody molecule to human tenascin-C comprising domain A1 may be determined. In some embodiments, the binding of the modified F16 antibody molecule to a sample obtained from an individual may be determined. In other embodiments, binding of the binding member to an antigen may be determined in in vivo, for example in imaging or detecting tumours in the body of an individual. The presence, location and/or amount of binding may be determined. Quantitation may be related to the amount of the antigen, which may be of diagnostic interest.

The binding of antibody molecules may be determined by any appropriate means. The mode of determining binding is not a feature of the present invention and those skilled in the art are able to choose a suitable mode according to their preference and general knowledge.

Preferred antibody molecules for use in such methods may be conjugated or linked to a reporter molecule or detectable label. Suitable detectable labels are described above. Binding may be determined by the presence, amount or localisation of the label or reporter.

Binding of a modified F16 antibody molecule in vivo, for example in a method of molecular imaging, may be determined by radioactive detection (e.g. PET, SPECT), near infrared fluorescence imaging (e.g. diffuse optical tomography, endoscopy), ultrasound (e.g. with targeted microbubble derivatives) and MRI (with targeted magnetic particles).

A method of detecting or diagnosing a proliferative disorder, such as a disease characterized by neovasculature, in an individual, may comprise:
  administering a modified F16 antibody molecule to the individual; and
  detecting binding of the antibody to neovasculature in the individual.
  wherein the binding of the antibody to neovasculature of the individual indicates that the individual has said disease.

Modified F16 antibody molecules may be useful in detecting or diagnosing a disease characterized by bone marrow neovasculature, such as leukaemia, myelodysplastic syndromes, or multiple myeloma, in an individual. For example, a method may comprise:
  administering a modified F16 antibody molecule to the individual; and
  determining the presence or absence of the antibody molecule in the bone marrow of the individual.

Modified F16 antibody molecules may be useful in detecting or imaging tumor cells or atherosclerotic plaques. An in vivo method of detecting and/or imaging tumour cells or atherosclerotic plaques may comprise:
  administering an modified F16 antibody molecule to an individual and
  detecting the binding of said antibody to tumour cells or atherosclerotic plaques in said individual.

In other embodiments, binding of the antibody may take place in vitro, for example in ELISA, Western blotting, immunocytochemistry, immuno-precipitation or affinity chromatography.

An in vitro method of detecting or diagnosing a proliferative disorder, such as a disease characterized by neovasculature, or an atherosclerotic disorder in an individual, may comprise:
  applying a modified F16 antibody molecule to a sample obtained from an individual; and
  detecting binding of the antibody to the sample,
  wherein the binding of the antibody to the sample indicates that the individual has said disease.

An in vitro method of detecting and/or imaging tumour cells may thus comprise contacting an antibody as described herein with a sample obtained from an individual and detecting the binding of said antibody to tumour cells in said sample.

Neovasculature may include bone marrow neovasculature. A disease characterized by bone marrow neovasculature may include such as leukaemia, myelodysplastic syndromes, or multiple myeloma. A method may comprise:
applying a modified F16 antibody molecule to a bone marrow sample obtained from the individual; and
detecting binding of the modified F16 antibody molecule to the sample,
wherein binding of the a modified F16 antibody molecule to bone marrow neovasculature in the sample indicates that the individual has said disease.

Other aspects and embodiments of the invention provide the aspects and embodiments described above with the term "comprising" replaced by the term "consisting of" and the aspects and embodiments described above with the term "comprising" replaced by the term "consisting essentially of".

Further aspects and embodiments of the invention will be apparent to those skilled in the art given the present disclosure including the following experimental exemplification.

Unless stated otherwise, antibody residues are numbered herein in accordance with the Kabat numbering scheme (Kabat, E. A., Wu, T. T., Perry, H. M., Gottesmann, K. S & Foeller, C. (1991). Sequences of Proteins of Immunological Interest, 5th edit., NIH Publication no. 91-3242. US Department of Health and Human Services.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

Certain aspects and embodiments of the invention will now be illustrated by way of example and with reference to the figures described above.

EXAMPLES

Materials and Methods

Cloning, Production and Purification of IgG(F16)-3S-N88Q

Primers were designed, in order to mutate the Asparagine 88 residue on IgG(F16)-3S light chain into Glutamine. Two 40 μL PCR reactions were prepared, using 20 μL of 2× ReadyMix REDTaq (R2648, ex. Sigma-Aldrich), 650 ng DNA Template (plasmid pMM137 containing IgG(F16)-3S sequence), 2 μL of 10 nM forward primer, 2 μL of 10 nM reverse primer and mQ water was added to reach a final volume of 40 μL. As primers, F16SpeILedSeqFo (SEQ ID NO: 8) and F16LCN88QRev (SEQ ID NO: 9) were used in reaction A, while F16LCN88QFo (SEQ ID NO: 10) and F16EcoRIRev (SEQ ID NO: 11) in reaction B. PCR amplification was carried out using the following program: 4 min at 94° C., 27 cycles: 20 s at 94° C., 45 s at 60° C., 2 min at 72° C., final extension 10 min at 72° C. Amplified samples were loaded on a 1% (w/v) Agarose/TBE buffer gel containing Ethidium Bromide solution (Ser. No. 10/714,181, ex. Fisher Scientific) diluted 1/10000. DNA fragments were separated under a constant current of 100 V and 70 mA for 35 min. Fragments of the desired size (355 bp for reaction A and 414 bp for Reaction B) were excised and purified using NucleoSpin Gel Clean-up (740609.250, ex. Macherey-Nagel), following supplier instructions. A second PCR reaction was set up, using 20 μL 2× ReadyMix REDTaq, about 80 ng of fragments from reaction A and B, 2 μL of F16SpeILedSeqFo primer, 2 μL of F16EcoRIRev primer and mQ water to reach a final volume of 40 μL. The same PCR program as depicted above was used and the desired fragment, containing the whole light chain mutated sequence (mutated LC; 730 bp), was gel-purified as explained previously.

The purified DNA fragment was digested in 1× CutSmart buffer (supplied with restriction enzymes, diluted in reaction volume and mQ water) for 2 h at 37° C., using 20 Units of each restriction enzyme (10× enzyme excess). At the same time, about 13 μg of pMM137 plasmid were digested using 5× enzyme excess under the same reaction conditions. SpeI-HF (R3133S, ex. NEB) and EcoRI-HF (R3101S, ex. NEB) were used to digest both fragment and plasmid. Digestion reaction was stopped with 1× Purple Gel Loading Dye (supplied with restriction enzymes), digested DNA fragments were separated on 1% (w/v) Agarose/TBE buffer gel and purified as described previously.

A 20 μL ligation reaction was prepared, using 530 ng insert-fragment (mutated-LC), 1 μg digested plasmid (1:5 vector:insert molar ratio), 2 μL of 10× T4 Ligase buffer (supplied with enzyme), 2 μL T4 DNA Ligase enzyme (M0202S, ex. NEB) and mQ water to reach final volume. Sample was incubated 15 min at room temperature (RT) and reaction was stopped by 10 min incubation at 65° C. 10 μL of both ligation reaction, as well as 10 μL of a 10× and 10 μL of a 50× dilution of the ligation reaction were gently mixed to 50 μL of TG1 electrocompetent E. coli cells in a Gene Pulser 0.2 cm cuvette (1652086, ex. Bio-Rad) on ice. Cells were transformed by electroporation using a BTX ECM600 Electro Cell Manipulator (Harvard Apparatus). A voltage of 1.2 kV was applied across the cuvette. 70 μL fresh 2xYT (3012-041, ex MPbio) medium were added to each transformation sample and each sample was plated on a 2xYT-Agar plate containing 1 μg/mL ampicillin. Plates were incubated at 37° C. overnight. 14 colonies were picked up with a toothpick from the 50× dilution-plate and inoculated in 4 mL 2xYT-ampicillin medium on a shaker at 37° C. for 5-7 h. Glycerol-stocks of the 14 cultures were prepared by mixing 400 μL culture with 400 μL 40% (v/v) glycerol/water and then stored at −20° C. Before inoculation in medium, each toothpick was dipped in a PCR sample containing 10 μL 2× ReadyMix REDTaq, 1 μl of F16SpeILedSeqFo primer, 1 μL of F16EcoRIRev primer and 8 μL mQ water and PCR amplification of the LC-coding sequence was carried out using the following program: 4 min at 94° C., 25 cycles: 20 s at 94° C., 45 s at 60° C., 80 s at 72° C., final extension 10 min at 72° C. PCR products were separated by Agarose-gel electrophoresis as already described and resulting LC-coding fragments were purified using NucleoSpin Gel Clean-up. Six of these purified fragments (derived from 6 different clones) were sent for sequencing and three of them were confirmed to contain the desired mutated-LC sequence. 400 µl of glycerol-stocked TG1 electrocompetent E. coli transformed with plasmid containing N88Q-mutated IgG(F16)-3S were inoculated in 4 mL 2xYT medium (containing 1 µg/mL ampicillin. After an incubation of 7 h in a shaker at 37° C.×150 rpm, the cultures were transferred in 400 mL fresh 1 µg/mL ampicillin/2xYT medium and the incubation continued o/n under the same conditions. The plasmids were purified using NucleoBond® Xtra Maxi Plus kit (740416.50, ex Macherey-Nagel) following the supplied protocol for low-copy plasmid and the concentration of the recovered plasmids was measured at 260 nm using Nano-Drop 2000c Spectrophotometer (Thermo Scientific).

PEI mediated transfections of different sizes, depending on the amount of antibody needed, were performed following the same protocol.

CHO-S cells (R800-07, ex Invitrogen) in PowerCHO-2CD$^+$ medium (BE12-771Q, ex Lonza) were counted and a culture volume containing the desired number of cells was centrifuged at room temperature using a Megafuge 1.0R centrifuge (5'×1000 rcf). Cells were resuspended in ProCHO-4$^+$ medium (BE12-029Q, ex Lonza) to a final concentration of 2×10$^6$ cells/mL.

The desired amounts of plasmid (1.25 µg/million cells) and polyethylenimine (PEI, 23966, ex. Polysciences Inc.) (5 µg/million cells, from a stock solution of 1 mg/mL) were separately diluted in 150 mM NaCl/H$_2$O (volume of DNA-NaCl resp. PEI-NaCl solutions equal ¹⁄₂₀ of the volume of ProCHO-4$^+$ medium), the DNA-NaCl solution was carefully mixed with the PEI-NaCl solution and the mixture was let stand for 10' to enable the formation of DNA-PEI complexes. The mixture was carefully added to cells, which were incubated on shaker at 37° C.×160 rpm for 4 h. PowerCHO-2CD$^+$ was added to the culture in order to dilute cells 1:2 and the culture was shaked at 31° C.×140 rpm for 5-7 days.

5-7 days culture was centrifuged using a Sorvall® RC 5C Plus centrifuge (SLA-3000 rotor, 4° C., 6500 rpm, 25'), supernatant was harvested and loaded on the pump connected to the PD-10 column and Protein A column. Flow rate of the pump was adjusted to 2 mL/min, supernatant was allowed to flow through and flow was stopped as soon as the descending level of supernatant reached the Protein A resin. PD-10 column was discarded and >200 mL of wash buffer A (100 mM NaCl, 0.5 mM EDTA, 0.1% (v/v) Tween-20 in PBS) first, and wash buffer B (500 mM NaCl, 0.5 mM EDTA in PBS) next, were loaded directly on protein A column at a higher flow rate (up to 7 ml/min), being careful not to let the protein A resin dry out. IgG proteins were eluted with 10-15 mL of 0.1M glycine/H$_2$O (pH 3) in fractions of 1 mL. OD$_{280}$ of every fraction was measured with NanoDrop 2000c Spectrophotometer (Thermo Scientific) in order to select fractions containing proteins. Positive fractions were pooled and loaded on Spectra/Por® 4 Dialysis Membrane MWCO 12-14 kDa (132700, ex Spectrum laboratories) previously wet in deionized water and sealed with plastic clips. Dialysis was carried out overnight in 3.5 L PBS. After dialysis OD$_{280}$ was measured again, proteins were concentrated to a final concentration of about 1 mg/mL using Vivaspin® Turbo 15 (VS15T01, ex Sartorious), sterile filtered using a 0.22 urn filter (99722, ex. TPP), aliquoted, flash-frozen in liquid nitrogen and stored at −80° C.

The desired amount of IgG was reduced with 30 molar equivalents of TCEP (AB121644, ex abcr), from a 0.1M TCEP/PBS stock solution, either overnight at 4° C. or 1 h at 37° C. The solution was loaded on Äkta FPLC (GE Healthcare) and the reduced protein was purified by size exclusion chromatography on a HiPrep 26/10 Desalting column (17-5087-01, ex. GE Healthcare). 1 mM DTPA (D6518, ex Sigma-Aldrich)/PBS was used as a mobile phase at a flow rate of 1.5-2 mL/min. The recovered protein was pooled and concentrated using Vivaspin® Turbo 15 (VS15T01, ex Sartorious) in order to remain in the capacity limit of the FPLC-loop. 10 molar equivalents of Vedotin (MC-vc_PAB-MMAE, ex. Concortis Biosystems) were dissolved in DMSO (41640, ex Sigma-Aldrich) and added to the reduced protein; final DMSO content was 5% (v/v). IgG and Vedotin were let react under stirring for 15' at RT, the reaction was then quenched with L-Cys (30090, ex Fluka) at a final concentration of 1 mM for 10' at RT. Final product was FPLC-purified as described previously, OD$_{280}$ was measured and the product was concentrated using Vivaspin® Turbo 15 (VS15T01, ex Sartorious) to about 1 mg/mL. Sterile-filtered aliquots were flash-frozen in liquid nitrogen and stored at −80° C. for further use.

SDS-PAGE

Protein samples were diluted to 0.2-0.3 mg/mL in PBS and mixed with either reducing or non-reducing 5× Loading buffer. Samples were denatured 5' at 95° C. and loaded on NuPAGE 4-12% Bis-Tris Gel (NP0335, ex. Novex by Life Technologies). 1×MES NuPAGE (NP0002, ex. Novex by Life Technologies) was used as running buffer and electrophoresis was performed at 180 V, 110 mA for 1 h. Gel was rinsed with deionized water and stained in Coomassie blue for 15-20' on an orbital shaker. Staining solution was discarded and the gel was rinsed 3 times with deionized water and immerged in destaining solution (10% acetic acid/30% methanol/mQ water) for 3-12 h on an orbital shaker. Destaining solution was discarded and recycled, gel was rinsed with deionized water and a picture of the gel was taken.

Recipes for the 5× Loading buffer and Coomassie blue stain are as follows:

| 100 ml, 5X non-red Loading Buffer | |
| --- | --- |
| Tris-HCl (250 mM, pH 6.8) | 20.8 mL |
| glycerol | 33.3 mL |
| SDS | 6.6 g |
| bromophenol blue | 66 mg |
| mQ water | up to 100 mL |

For 5× reducing Loading buffer, add 5-10% (v/v) 2-mercaptoethanol

| 1 L Coomassie blue | |
| --- | --- |
| PlusOne Coomassie PhastGel Blue R-350 | 2 tablets |
| H2O | 500 mL |
| Methanol | 400 mL |
| Acetic acid | 100 mL |

PNGase F Protocol

12 µL of a 1.6 mg/mL IgG(F16)-3S sample (about 19 µg of glycoprotein) were mixed with 2 µL of 10× Glycoprotein Denaturing Buffer (reagent supplied with PNGase F enzyme) and 6 µL. of mQ water. The mixture was incubated 8' at 95° C. to denature the glycoprotein, briefly chilled on ice and centrifuged for 10'. 4 µL of 10× Glycobuffer 2, 4 µL of 10% NP-40 (reagents supplied with PNGase F enzyme), 12 µL of mQ water and finally 2 µL of PNGase F enzyme (P0704, ex. NEB) were added to the sample, which was gently mixed and incubated 1 h at 37° C. After the incubation half of the sample (20 µL) was mixed with reducing 5× Loading buffer, while the other half with non-reducing 5×

Loading buffer and samples were analyzed by SDS-PAGE. 1×MOPS NuPAGE (NP0001, ex. Novex by Life Technologies) was used as running buffer instead of 1×MES.

Size Exclusion Chromatography (SEC)

100 μL of diluted sample (final concentration 0.3-0.5 mg/mL) were loaded on FPLC (Äkta, GE Healthcare) and protein were separated by a Superdex200 10/300GL column (GE Healthcare) previously equilibrated with 1 CV PBS, using PBS as mobile phase at a flow rate of 0.5 mL/min (column pressure limit set at 1.5 MPa). Proteins were detected by an UV-detector at a wavelength of 280 nm.

Liquid Chromatography-Mass Spectrometry (LC-MS)

Samples were diluted to about 0.1 mg/mL and LC-MS was performed on a Waters Xevo G2-XS Qtof instrument (ESI-ToF-MS) coupled to a Waters Acquity UPLC H-Class System using a 2.1×50 mm Acquity BEH300 C4 1.7 μm column (186004495, ex. Waters). 0.1% formic acid in water (solvent A) and 0.1% formic acid in acetonitrile (solvent B) were used as mobile phase at a flow rate of 0.4 mL/min. Gradient was programmed as follows: after 1.5 min isocratic with 95% solvent A, stepwise change from 95% solvent A to 95% solvent B in 4.5 min (10% increase every 0.5 min), back to 95% solvent A in 0.5 min, linearly to 95% solvent B and back to 95% solvent A in 2.25 min (last step repeated twice).

Surface Plasmon Resonance (SPR)

A new CM5 Sensor Chip (BR100012, ex. GE Healthcare) was primed for about 1 h with HBS-EP buffer (BR100188, ex. GE Healthcare) at a flow rate of 2 μL/min. The carboxymethylated dextran matrix of the chip was activated with 40 μL of a 1:1 mixture of 400 mM EDC-HCl and 100 mM NHS and coated with 30 μL of 50 μg/mL hTnC A1 (received from Philochem) in either Acetate 4.5 buffer (BR100350, ex. GE Healthcare) or Acetate 5 buffer (BR100351, ex. GE Healthcare). Residual, activated carboxylic acids of the matrix were quenched with 30 μL of 1M ethanolamine and unbound proteins were flushed away with 10 μL of 10 mM HCl. Coated chip was primed with 0.01% (w/v) NaN$_3$ in PBS at a flow rate of 5 μL/min. 30 μL samples were injected at a flow rate of 10 μL/min, followed by 300s of buffer flow (dissociation phase). Chip was washed before and after every sample injection with 5-10 μL. of 10 mM HCl.

ELISA Assay

24× Maxisorp Nunc-Immuno wells (468667, ex. Thermo Scientific) were coated with 100 μl of 1×10$^{-7}$M alternative-spliced domain A1 of human Tenascin C (hTnC A1, received from Philochem) in PBS o/n at 4° C. Wells were washed 3 times with PBS and blocked for 1 h at RT with 200 μL 2% (w/v) milk powder (ex. coop) in PBS. Blocking solution was discarded and wells were washed 3 times with PBS. Each well was filled with 88 μL of protein samples at different concentrations, diluted in 2% milk-powder/PBS and the plate was incubated 1 h at RT. PBS, SIP(KSF) and IgG(F8) were used as negative controls. Protein solutions in the wells were discarded and the wells washed 3 times with PBS then incubated 1 h at RT with 100 μL of a 1/1000 dilution of protein A-HRP (NA9120V, ex. GE Healthcare) in 4% (w/v) milk powder/PBS. After discarding content of wells and washing 3 times with PBS-Tween (PBS+0.05% (v/v) Tween 20) and 3 times with PBS, 100 μL of BM Blue POD Substrate (11484281001, ex. Roche) were added to each well. Reaction was stopped after 5' by adding 50 μL of 1M H$_2$SO$_4$ to each well and absorbance at 450 nm was measured.

Tumor Cell Culture

Cells of three different human-derived tumors; U-87 glioblastoma cells (HTB-14, ex ATCC), A-431 epidermoid carcinoma cells (CRL-1555, ex ATCC) and MDA-MB-231 adenocarcinoma cells (HTB-26, ex ATCC) were cultured in culture flasks starting from aliquots stored in cryotubes. U-87 cells were cultured in MEM (41090-028, ex Life Technologies), while A-431 and MDA-MB-231 were cultured in DMEM (41966-029, ex Life Technologies). All media was supplemented with 10% (v/v) FBS (16000-044, Ex Gibco® by Life Technologies) and 1×Anti-Anti (15240-062, Ex Gibco® by Life Technologies). Cells were passaged from T75 to T150 and T300 upon reaching about 80% confluence; once in T300, cells were split in multiple T300 until reaching the desired number of cells needed for implantation into mice. Passaging/splitting procedure included discarding old medium, washing 1× with sterile PBS, detaching cells by incubation in 0.05% Trypsin-EDTA (25300-062, Ex Gibco® by Life Technologies) and adding pre-warmed fresh medium. 0.25% Trypsin-EDTA (15050-065, ex. Gibco® by Life Technologies) was used for detaching A-431 cells.

Tumor Implantation

Tumor cells were detached from T300 flask by trypsinization, diluted in fresh medium and counted. A volume containing the desired number of cells was centrifuged 5'×1000 rcf using Megafuge 1.0R (Heraeus Instruments). Pellet was resuspended in 50 mL HBSS (14175-053, Ex Gibco® by Life Technologies), centrifuged again and finally resuspended in about 500 HBSS; enough to inject five mice with 100 μL. Each MDA-MB-231 assigned mouse received 15×10$^6$ cells, each U-87 6.0×10$^6$ and each A-431 2.7×10$^6$ as a subcutaneous (s.c.) injection into the right flank.

Tumor size was measured using a digital caliper and volume was calculated using the following formula:

$$\text{Tumor size } [\text{mm}^3] = \frac{\text{length } [\text{mm}] \times \text{width}^2 [\text{mm}]}{2}$$

with length being the higher- and width the lower value.

Mice were sacrificed when tumor size reached 2000 mm$^3$ or weight loss exceeded 15% of the initial (pre-implantation) body weight. Experiments were conducted under a project license issued by the Veterinäramt des Kantons Zürich, Switzerland (Bew. Nr. 42/2012 and Nr. 027/15).

Therapy Experiment

Implanted tumors were let grow to an average volume of about 100 mm$^3$ before starting with therapy regimen. Three mice per tumor model received 7 mg/Kg IgG(F16)-3S-N88Q-Vedotin, three received 7 mg/Kg SIP(F16)-Vedotin and three received PBS, every 3 days, 4 times in total. Sterile-filtered solutions were injected intravenously into the lateral tail vein, using Omnican® 50 Insulin syringe (9151125, ex B. Braun).

Biodistribution Study

Biodistribution experiment was started when the tumors reached an average volume of 200-400 mm$^3$. At least 2 days before starting the experiment, mice were put on Lugol's solution 5% (3 drops for each full water bottle). Before starting with the labeling, mice were given an oral dose of sodium perchlorate (1 drop of a 1 g/mL sodium perchlorate solution in water).

Labeling of IgG(F16)-3S, N88Q-IgG(F16)-3S and SIP (F16)

Three Pierce Pre-Coated Iodination Tubes (28601, ex. Life Technologies) were wet with 1 mL sterile-filtered PBS for 5 min. PBS was removed and 100 μL of fresh PBS were added directly to the bottom of each tube. 1.5 μL of $I^{125}$ (NEZ033A001MC, ex. Perkin Elmer) were added to each tube, which was incubated 5 min at RT, under regular swirling (every 30 s). The resulting activated iodide was removed from the Pierce tube and added to 400 μL of protein diluted in PBS (three protein samples were prepared; wild-type IgG(F16)-3S [1.125 mg/ml], mutant IgG(F16)-3S [0.87 mg/ml] and SIP(F16) [0.88 mg/ml]). Samples were incubated 5 min at RT, under gentle swirling every 30 s. 496.5 μL of each sample were loaded on a PD-10 column (17-0851-01, ex. GE Healthcare), previously blocked with 1 mL of 1 mg/mL BSA/PBS and pre-equilibrated with 25 mL PBS. Samples were let penetrate into the column resin and 2 mL PBS were added to each PD-10 in order to reach the recommended input volume of 2.5 mL. Labeled proteins were eluted with 3 mL PBS. Fractions of 5 and 11 drops were collected in 5 Eppendorf tubes (5 drops for first fraction, 11 drops for subsequent ones). First fraction was discarded, while 5 μL of each remaining fraction were used for incorporation test.

Incorporation Test

Activity was measured in ten samples, in order to determine the average amount of radioactive iodine incorporated on proteins. Ten Counter vials (55.476, ex. Sarstedt) were prepared as described in Table 1.

TABLE 1

Counter vials preparation for incorporation test.

| Counter Vial | Content |
| --- | --- |
| 1 | 5 μL of labeling reaction sample, before loading on PD-10 + 1 mL PBS (1% of input) |
| 2 | 10 μL of vial 1 + 1 mL PBS |
| 3 | 5 μL of fraction 2 + 1 mL PBS (1% of fraction 2) |
| 4 | 10 μL of vial 3 + 1 mL PBS |
| 5 | 5 μL of fraction 3 + 1 mL PBS (1% of fraction 3) |
| 6 | 10 μL of vial 5 + 1 mL PBS |
| 7 | 5 μL of fraction 4 + 1 mL PBS (1% of fraction 4) |
| 8 | 10 μL of vial 7 + 1 mL PBS |
| 9 | 5 μL of fraction 5 + 1 mL PBS (1% of fraction 5) |
| 10 | 10 μL of vial 9 + 1 mL PBS |

Vials were analyzed on Cobra Auto-Gamma counter (Packard) and resulting values were used to calculate the incorporation efficiency, using the following formula:

$$\text{Incorporation Rate } \left[\frac{\text{cpm}}{\mu g}\right] = \frac{\text{sum of activities in vials 3, 5, 7, 9 [cpm]} \times 100}{\text{input protein } [\mu g] \times 0.8}$$

by assuming that 80% of protein was recovered after purification on PD-10.

Nine mice bearing the same tumor xenograft were equally divided in 3 groups; one group was assigned to SIP(F16), the second to wild-type IgG(F16)-3S and the third to IgG(F16) N88Q-3S. Each mouse in the group was injected with the corresponding labeled-protein. Only sample containing the main fraction of labeled protein was used for injections (about 150 μL/mouse). The Injected Dose was calculated with the following formula:

$$ID \text{ [cpm]} = \frac{\text{activity in 1\% of main fraction [cpm]}}{1\% \text{ of main fraction volume } [\mu L]} \times \text{injected volume } [\mu L]$$

After 24 h, mice were sacrificed and tumor and organs (liver, lungs, intestine, stomach, kidneys, heart, blood, spleen, tail) were resected and collected in pre-weighted Counter vials. Weight of tumor and organs was determined and their activity was measured on Cobra Auto-Gamma counter. Accumulation of the investigated protein in different organs and tumor was calculated with the following formula:

$$\% \frac{ID}{g} = \frac{\text{activity in organ [cpm]}}{ID \text{ [cpm]} \times \text{weight of organ [g]}} \times 100$$

Results

Figure 2:
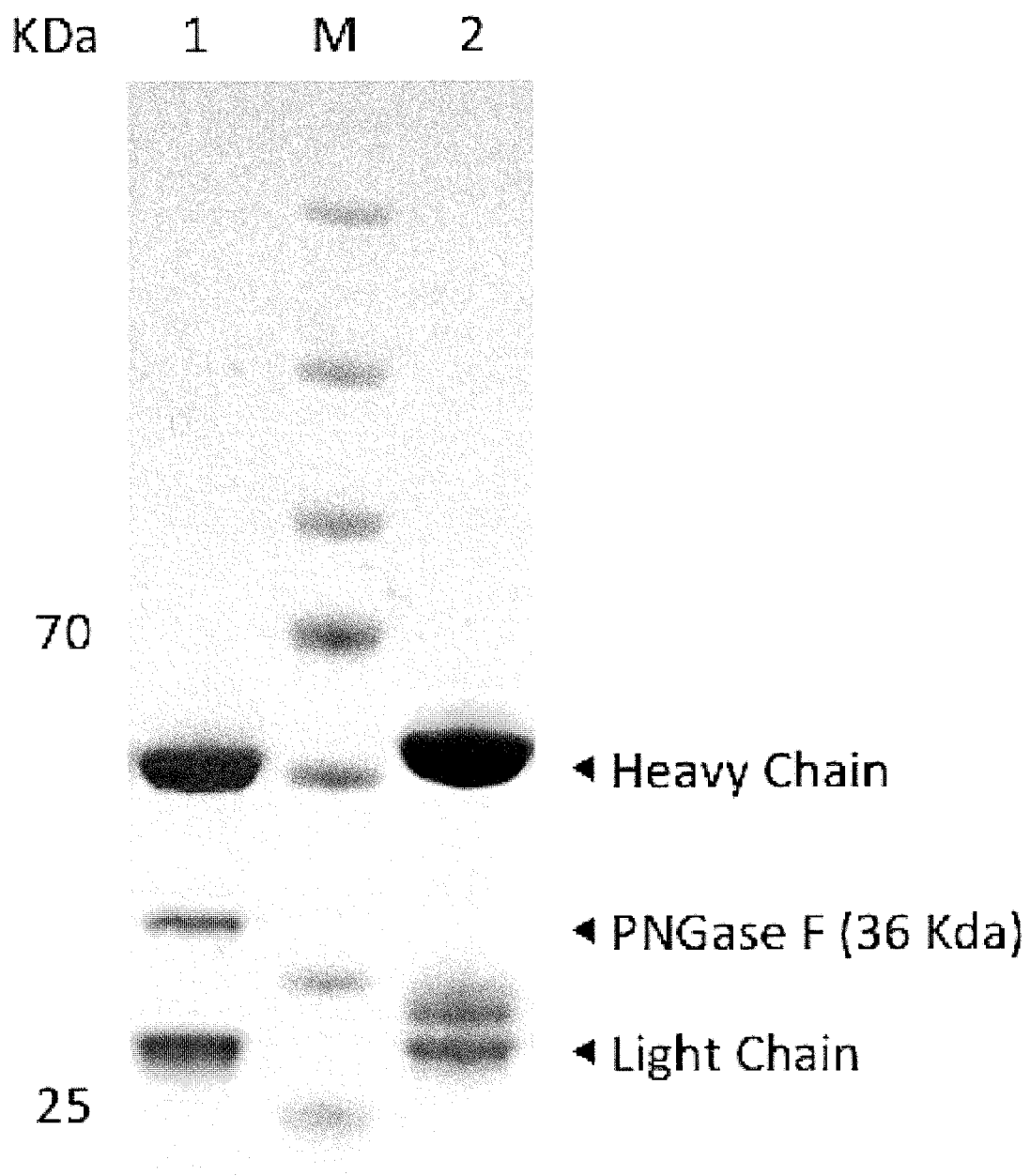
FIG. 2 shows the results of an SDS-PAGE analysis of the wild-type IgG(F16)-3S antibody before (lane 1) and after PNGase F treatment (lane 2) under reducing conditions. The location of the bands corresponding to the light and heavy chain and PNGase F is indicated. A difference in the weight of the glycosylated and deglycosylated light chain can be observed in the untreated sample in lane 2.

The mutant IgG(F16)N88Q-3S antibody exhibited favorable biochemical properties as confirmed using SDS-PAGE analysis, size exclusion chromatography and mass spectrometry. The SDS-PAGE analysis revealed the presence of only two distinct bands; one for the Heavy Chain and the other for the Light Chain (FIG. 1A), confirming that the produced mutant lacks glycosylation on its Light Chain. This is in accordance with the results previously achieved using PNGase F (FIG. 2).

Figure 1B:
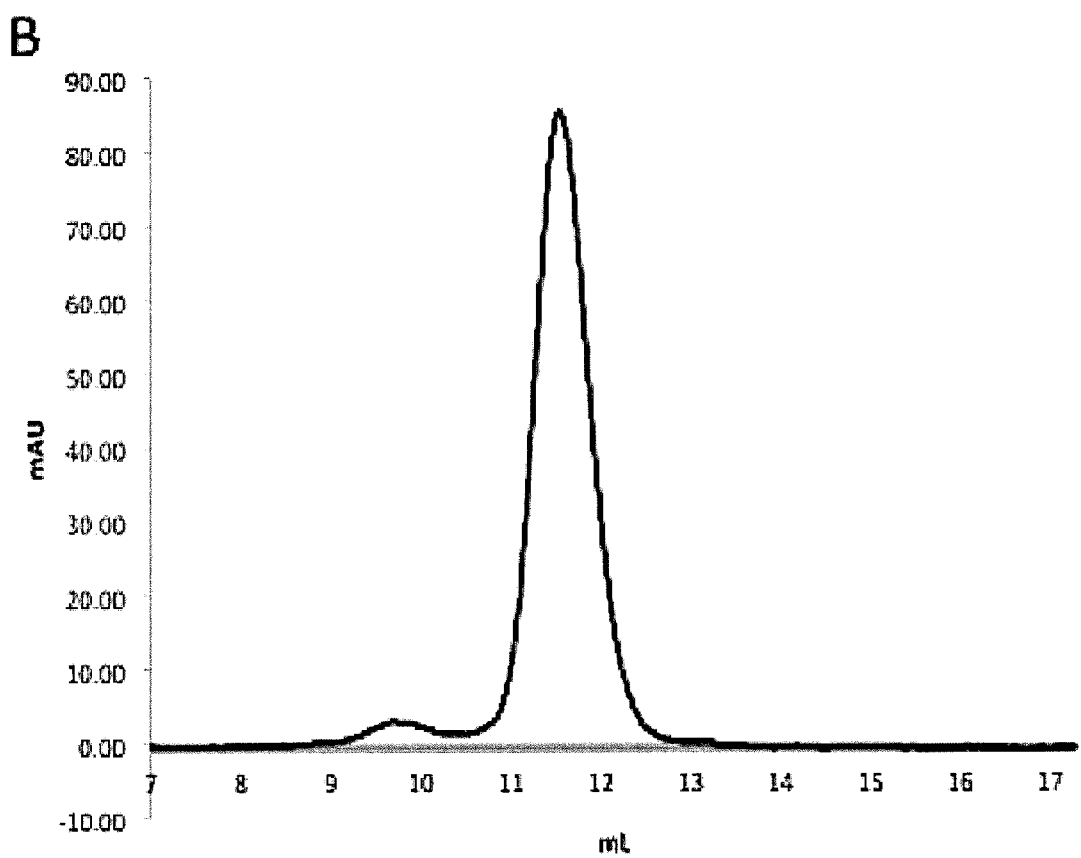
Figure 1C:
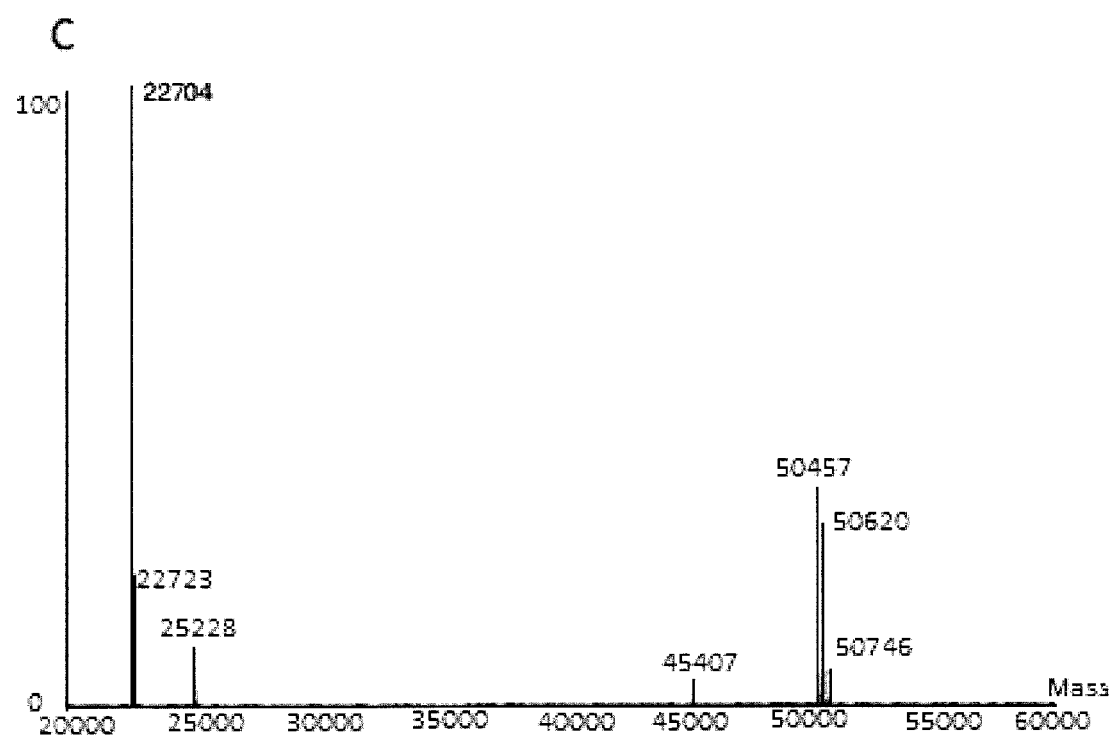

Size exclusion chromatography (FIG. 1B), analysis showed a product of good quality with little aggregate amount. Retention volume was on accordance with the size of an IgG. Mass spectrometry analysis (FIG. 1C) confirmed the absence of glycosylated Light Chain and with a measured mass (22704 Da) very close to the expected MW (22707 Da). The peaks around 50500 Da correspond to the glycosylated Heavy Chain.

Figure 3A:
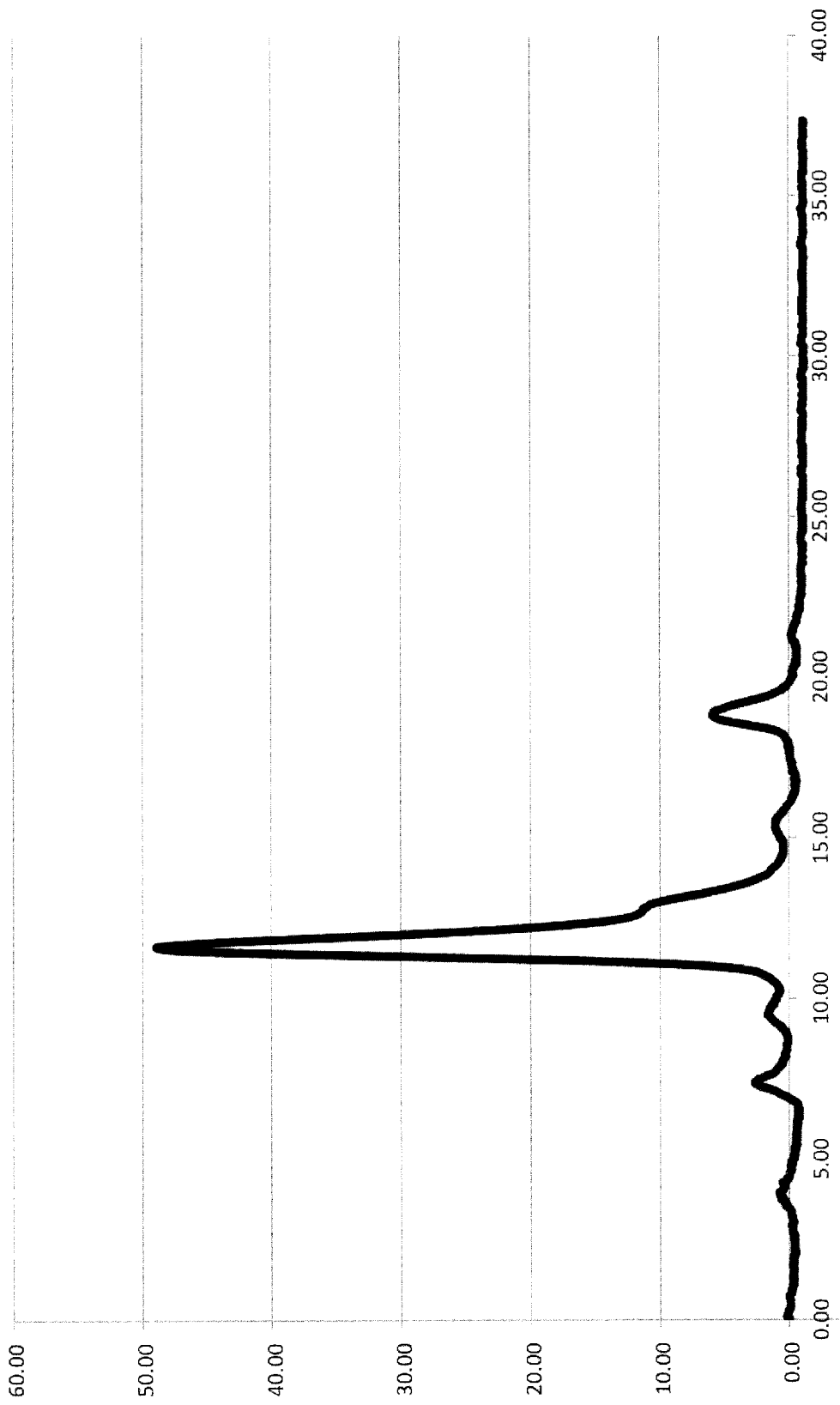
FIG. 3 shows the FPLC profile of the conjugates IgG(F16)-3S-MMAE (FIG. 3A) and IgG(F16)-3S-N88Q-MMAE (FIG. 3B).
Figure 3B:
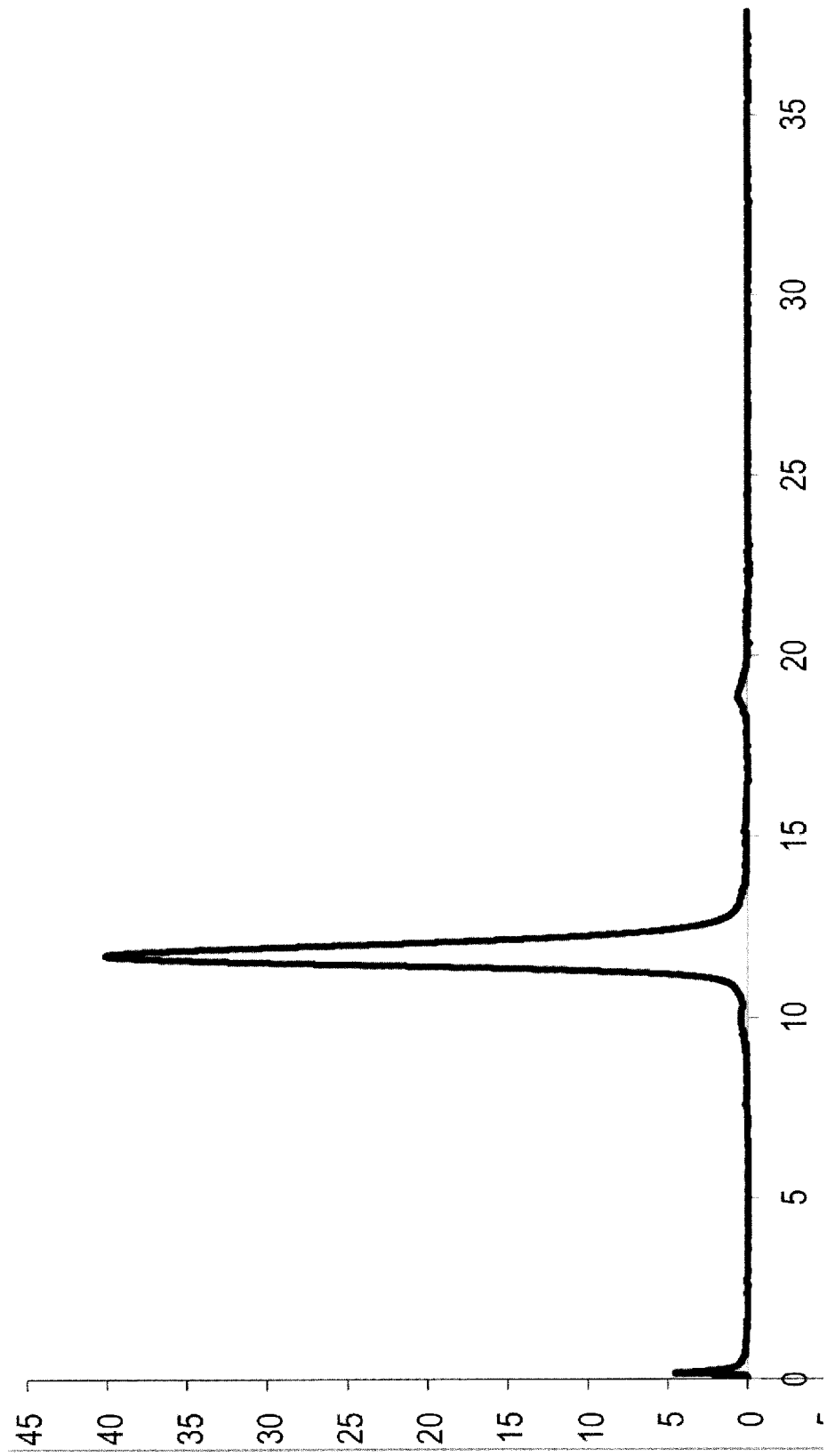

Fast protein liquid chromatography (FPLC: FIGS. 3A and 3B) showed that a glycosylated IgG(F16)-3S-MMAE conjugate (FIG. 3A) displayed more protein aggregation than an unglycosylated IgG(F16)N88Q-3S-MMAE conjugate (FIG. 3B).

Figure 4:
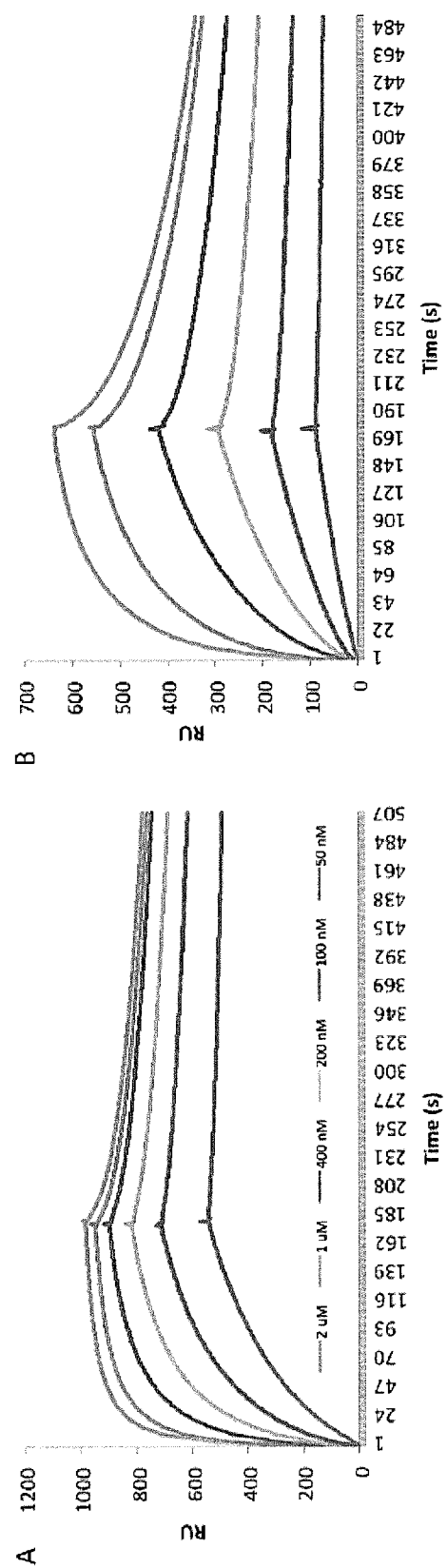
FIGS. 4A and 4B show the results of surface plasmon resonance (BIAcore) for the mutant IgG(F16)-3S-N88Q (FIG. 4A) and wild-type IgG(F16)-3S (FIG. 4B) antibody, respectively 50 nM curves were fitted to extrapolate apparent $K_D$ values.
Figure 5:
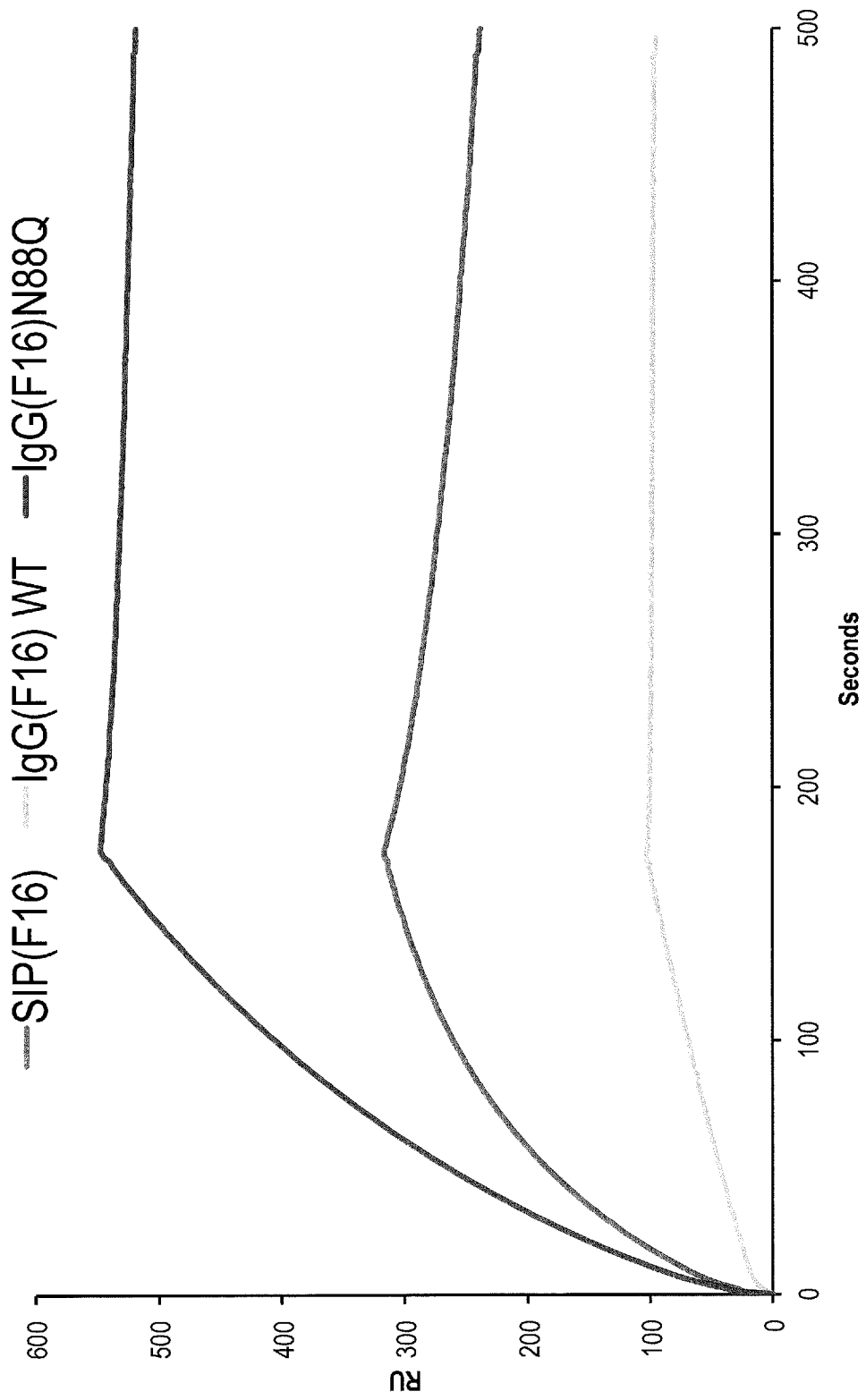
FIG. 5 shows the BIAcore curves of 50 nM wild-type IgG(F16)-3S, SIP(F16) and mutant IgG(F16)-3S-N88Q antibodies.

The ability of the mutant antibody to bind domain A1 of tenascin-C large isoform was compared with IgG(F16)-3S-WT and SIP(F16) using surface plasmon resonance (Biacore). SPR analysis showed a difference in affinity between mutant and wild-type IgG (FIG. 4 and FIG. 5). Upon fitting of the BIAcore curves, estimated apparent $K_D$ of the mutant was in the range of high picomolar to low nanomolar; about 4-8 times lower than that of the wild-type IgG (low nanomolar to two digit nanomolar). The fact that there is a significant affinity difference between the two IgGs was also evident under a qualitative point of view. As shown in FIG. 4 and FIG. 5, the shape of the curves is different and mutant-IgG was able to reach much higher RU values than wild-type IgG, reflecting the higher amounts of analytes which bind to the ligand. The mutant antibody also displayed improved binding affinity compared with the SIP (F16) antibody molecule.

Figure 6:
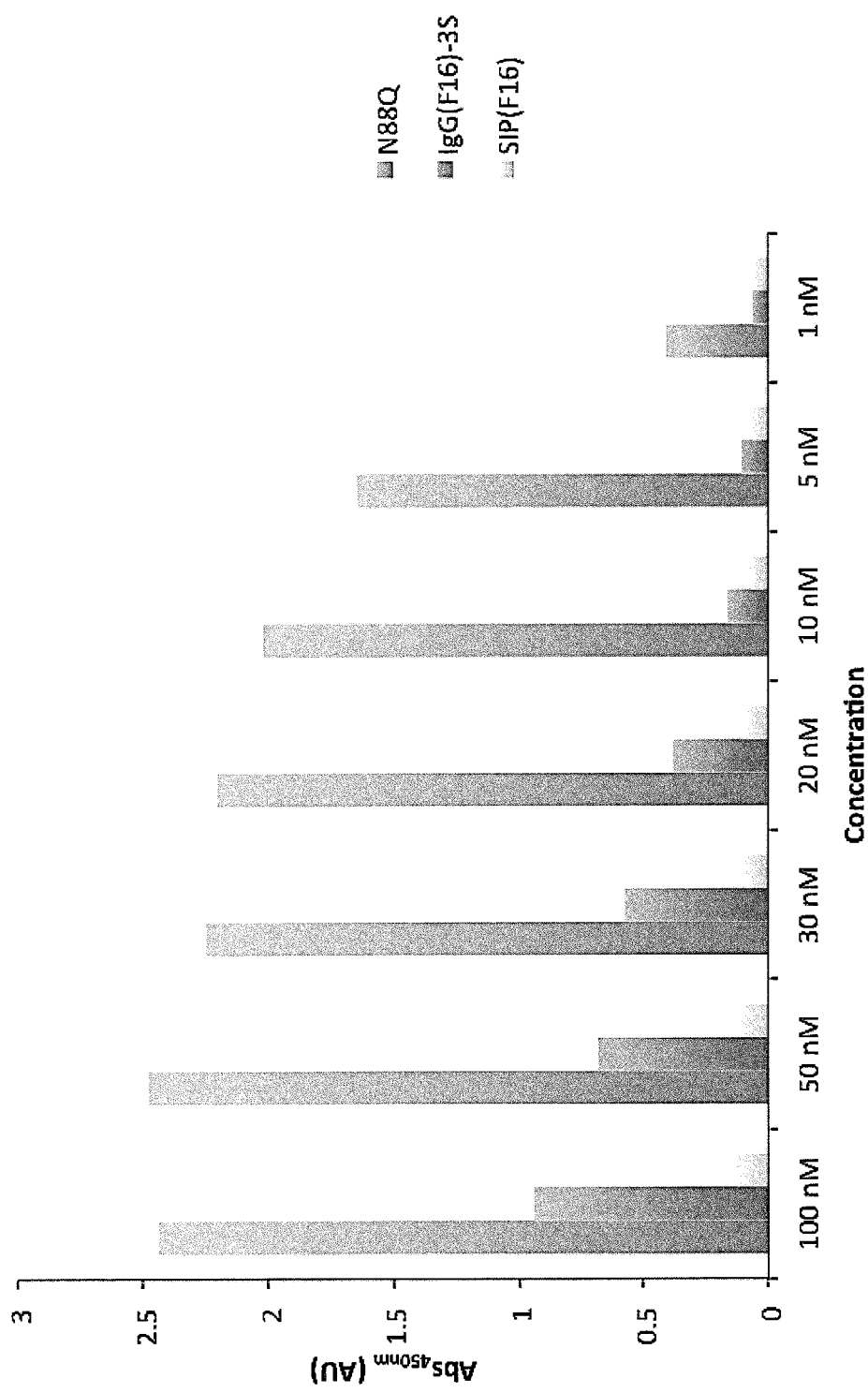
FIG. 6 shows the results of an ELISA analysis carried out using IgG(F16)-3S-N88Q, wild-type IgG(F16)-3S and SIP (F16). The results show that there is a difference in binding affinity between the mutant and wild-type IgGs.

Difference in affinity was further confirmed by ELISA analysis (FIG. 6). Different concentrations of mutant, wild-type IgG(F16)-3S and SIP(F16) were tested, revealing a discrepancy between signals deriving from mutant and signals deriving from wild-type protein.

Figure 7:
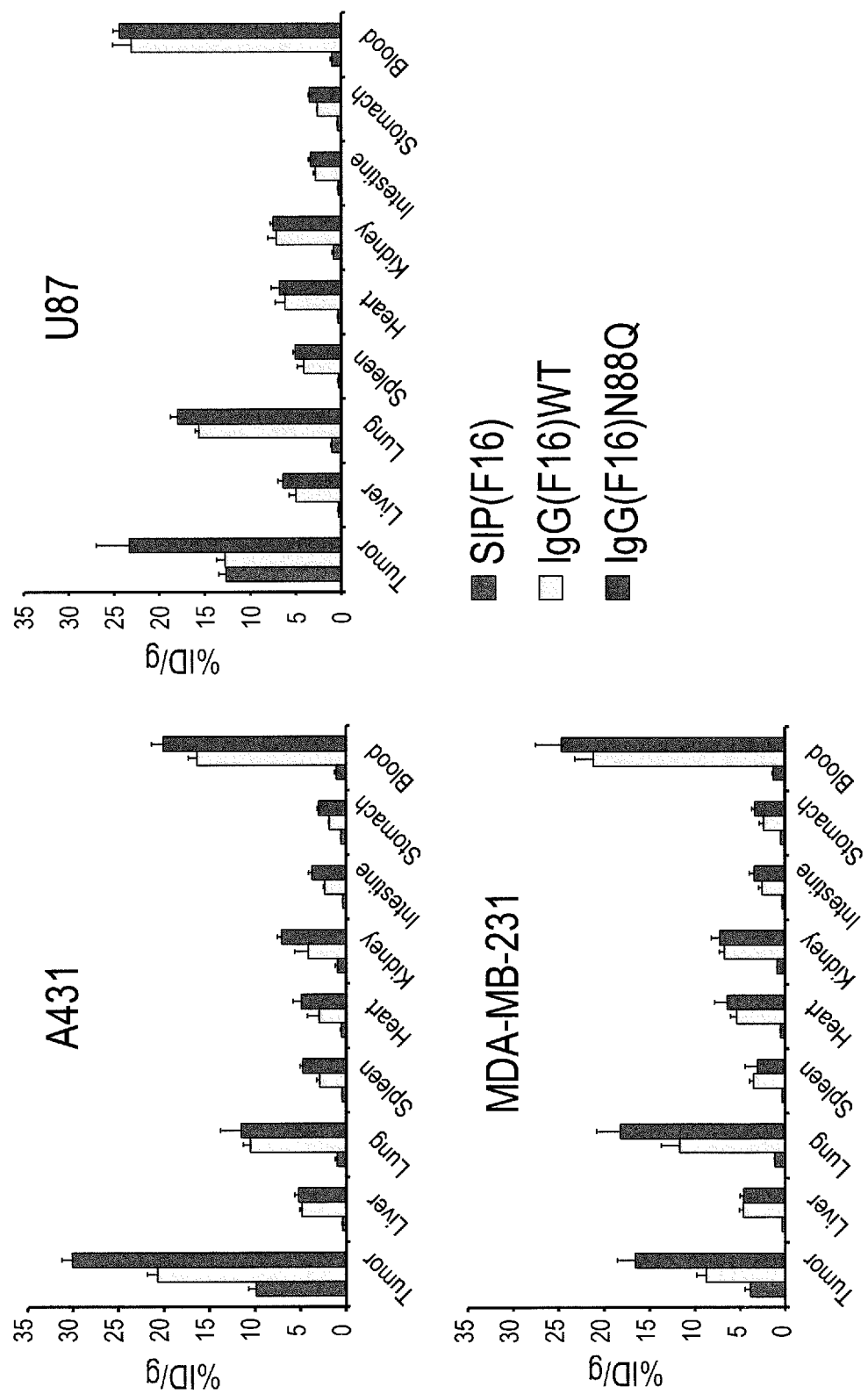
FIG. 7 shows the results from a biodistribution studies using the SIP(F16), wild-type IgG(F16)-3S and IgG(F16)-3S-N88Q antibodies in A-431, U87 and MDA-MB-231 tumor-bearing Balb/c nude mice. The y-axis shows the percentage of the injected dose of the antibody per gram of tissue (% ID/g).

Biodistribution analysis in 3 human models (U87/A431/MDA-MB-231) showed superiority of the IgG(F16)N88Q mutant over its wild-type counterpart with an increase of % ID/g in tumors of about 10% in all models (FIG. 7).

Figure 8:
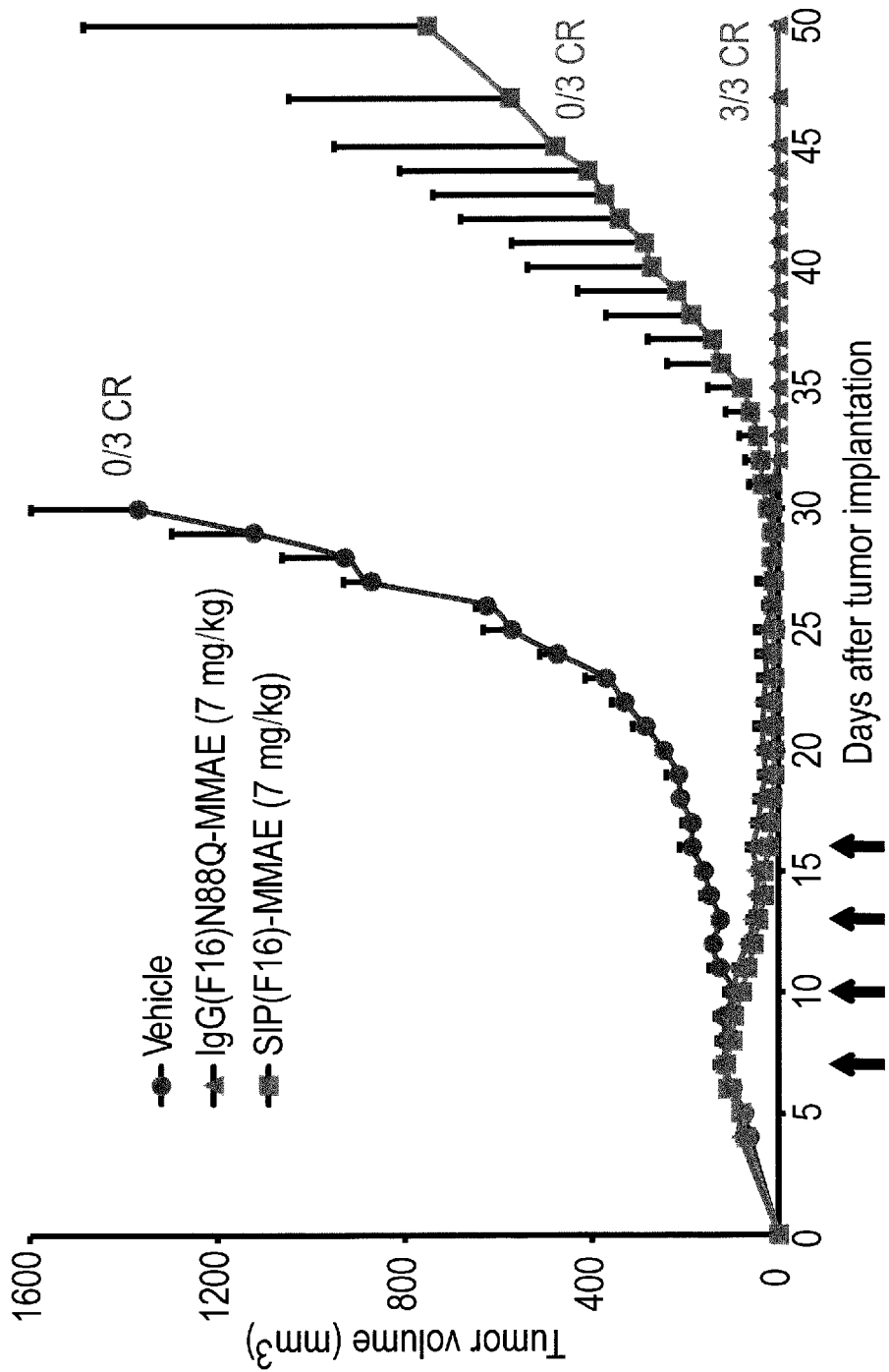
FIG. 8 shows the results from a therapy study in Balb/c nude mice bearing U87 glioblastoma model. Mice were injected with 7 mg/kg of either PBS, IgG(F16)N88Q-MMAE or SIP(F16)-MMAE as indicated and the tumor volume was measured. Data represents mean tumor volume (±SEM), n=3 mice per group. 'CR' indicates complete remission.
Figure 9:
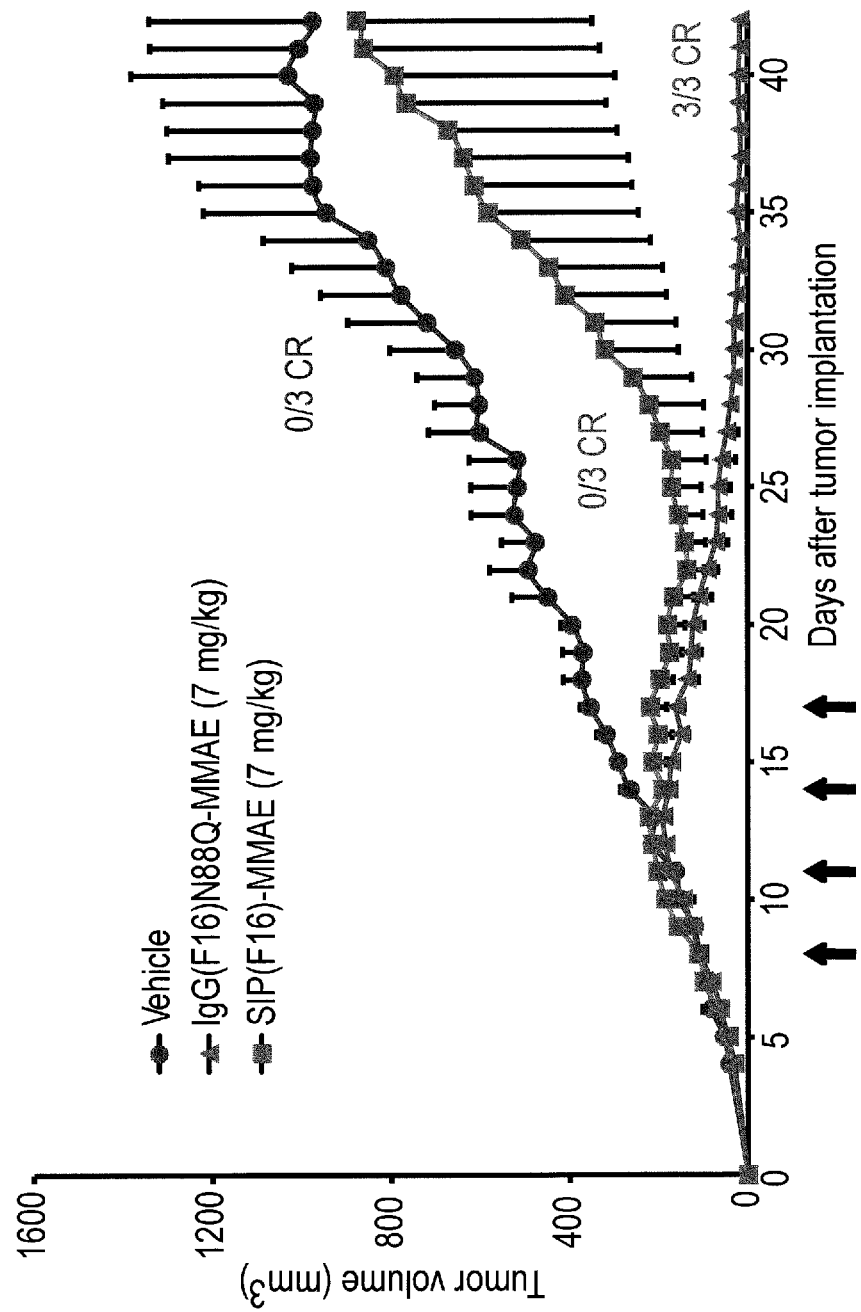
FIG. 9 shows the results from a therapy study in Balb/c nude mice bearing A431 epidermal carcinoma model. Mice were injected with 7 mg/kg of either PBS, IgG(F16)N88Q-MMAE or SIP(F16)-MMAE as indicated and the tumor volume was measured. Data represents mean tumor volume (±SEM), n=3 mice per group. 'CR' indicates complete remission.

In therapy studies, the MMAE conjugated version of IgG(F16)N88Q showed very good efficacy both in the U87 (FIG. 8) and A431 (FIG. 9) models. Using a dose of 7 mg/kg, every 3 days, 4 times in total, it was able to achieve complete and lasting cure in three out of three mice in the IgG(F16) N88Q-MMAE group.

```
                        Sequence Listing
SEQ ID NO: 1 - F16VH domain
EVQLLESGGG LVQPGGSLRL SCAASGFTFS RYGMSWVRQA PGKGLEWVSA ISGSGGSTYY
ADSVKGRFTI SRDNSKNTLY LQMNSLRAED TAVYYCAKAH NAFDYWGQGT LVTVSS SEQ ID NO: 2 - generic F16 VL domain
SSELTQDPAV SVALGQTVRI TCQGDSLRSY YASWYQQKPG QAPVLVIYGK NNRPSGIPDR
FSGSSSGNTA SLTITGAQAE DEADYYCX₁SX₂ VYTMPPVVFG GGTKLTVLG X₁ and X₂ are any amino acid except when X₁ is N, and X₂ is not S or T
SEQ ID NO: 3 - N88Q mutation F16 VL domain,
SSELTQDPAV SVALGQTVRI TCQGDSLRSY YASWYQQKPG QAPVLVIYGK NNRPSGIPDR
FSGSSSGNTA SLTITGAQAE DEADYYCQSS VYTMPPVVFG GGTKLTVLG N to Q substitution highlighted
SEQ ID NO: 4 - WT F16 light chain
SSELTQDPAV SVALGQTVRI TCQGDSLRSY YASWYQQKPG QAPVLVIYGK NNRPSGIPDR
FSGSSSGNTA SLTITGAQAE DEADYYCNSS VYTMPPVVFG GGTKLIVLGQ PKAAPSVTLF
PPSSEELQAN KATLVCLISD FYPGAVTVAW KADSSPVKAG VETTTPSKQS NNKYAASSYL
SLTPEQWKSH KSYSCQVTHE GSTVEKTVAP TECS Glycosylation site highlighted
SEQ ID NO: 5 - F16 Heavy chain
EVQLLESGGG LVQPGGSLRL SCAASGFTFS RYGMSWVRQA PGKGLEWVSA ISGSGGSTYY
ADSVKGRFTI SRDNSKNTLY LQMNSLRAED TAVYYCAKAH NAFDYWGQGT LVTVSSASTK
GPSVFPLAPS SKSTSGGTAA LGCLVKDYFP EPVTVSWNSG ALTSGVHTFP AVLQSSGLYS
LSSVVTVPSS SLGTQTYICN VNHKPSNTKV DKKVEPKSSD KTHTSPPSPA PELLGGPSVF
LFPPKPKDTL MISRTPEVTC VVVDVSHEDP EVKFNWYVDG VEVHNAKTKP REEQYNSTYR
VVSVLTVLHQ DWLNGKEYKC KVSNKALPAP IEKTISKAKG QPREPQVYTL PPSRDELTKN
QVSLTCLVKG FYPSDIAVEW ESNGQPENNY KTTPPVLDSD GSFFLYSKLT VDKSRWQQGN
VFSCSVMHEA LHNHYTQKSL SLSPGK SEQ ID NO: 6 - N88Q F16 light chain
SSELTQDPAV SVALGQTVRI TCQGDSLRSY YASWYQQKPG QAPVLVIYGK NNRPSGIPDR
FSGSSSGNTA SLTITGAQAE DEADYYCQSS VYTMPPVVFG GGTKLTVLGQ PKAAPSVTLF
PPSSEELQAN KATLVCLISD FYPGAVTVAW KADSSPVKAG VETTTPSKQS NNKYAASSYL
SLTPEQWKSH KSYSCQVTHE GSTVEKTVAP TECS N to Q substitution highlighted
SEQ ID NO: 7 - WT F16 VL domain
SSELTQDPAV SVALGQTVRI TCQGDSLRSY YASWYQQKPG QAPVLVIYGK NNRPSGIPDR
FSGSSSGNTA SLTITGAQAE DEADYYCNSS VYTMPPVVFG GGTKLTVLG Glycosylation site highlighted
SEQ ID NO: 8 - F16SpeILedSeqFo SDM primer
CAGAGTAGTGTCGACCATGGGCTGGAGCCTGATCCTGCTGTTCCT SEQ ID NO: 9 - F16LCN88QRev SDM primer
CATAGTATAAACAGAGGATTGACAGTAATAGTCAGCCTC SEQ ID NO: 10 - F16LCN88QFo SDM primer
GAGGCTGACTATTACTGTCAATCCTCTGTTTATACTATG SEQ ID NO: 11 - F16EcoRIRev SDM primer
CAGGAATTCTTACTATGAACATTCTGTAGGGGCGACTGTCTTCTC SEQ ID NO: 12 - Human IL-2 amino acid sequence - mature sequence
APTSSSTKKT QLQLEHLLLD LQMILNGINN YKNPKLTRML TFKFYMPKKA TELKHLQCLE
EELKPLEEVL NLAQSKNFHL RPRDLISNIN VIVLELKGSE TTFMCEYADE TATIVEFLNR
WITFCQSIIS TLT
```

The invention claimed is:

1. An antibody molecule that binds human tenascin-C comprising:
   (a) a heavy chain variable (VH) domain comprising the amino acid sequence of SEQ ID NO: 1; and
   (b) a light chain variable (VL) domain comprising the amino acid sequence of SEQ ID NO: 7 with an Asn to Gln substitution at position 88.

2. An antibody molecule according to claim 1 wherein the VL domain comprises the amino acid sequence of SEQ ID NO: 3.

3. An antibody molecule according to claim 1 comprising:
   (a) a heavy chain comprising the amino acid sequence of SEQ ID NO: 5, or an amino acid sequence having less than 5 sequence alterations relative to SEQ ID NO: 5; and
   (b) a light chain comprising the amino acid sequence of SEQ ID NO: 6 or an amino acid sequence having less than 5 sequence alterations relative to SEQ ID NO: 6.

4. An antibody molecule according to claim 1 which binds to the A1 domain of tenascin C with a higher affinity than an antibody comprising the VH domain of SEQ ID NO: 1 and the VL domain of SEQ ID NO: 7.

5. An antibody molecule according to claim 1 which displays;
   (i) reduced aggregation
   (ii) increased efficacy and/or
   (iii) increased tumor biodistribution
   relative to the corresponding antibody molecule comprising the VH domain of SEQ ID NO: 1 and the VL domain of SEQ ID NO: 7.

6. An antibody molecule according to claim 1 which is a whole antibody.

7. An antibody molecule according to claim 6 which is an IgG.

8. An antibody molecule according to claim 1 wherein the antibody molecule is conjugated to a bioactive molecule.

9. An antibody molecule according to claim 8 wherein the bioactive molecule is a cytotoxic agent.

10. An antibody molecule according to claim 8 wherein the bioactive molecule is a cytokine.

11. An antibody molecule according to claim 10 wherein the cytokine is IL-2.

12. An isolated nucleic acid molecule encoding an antibody molecule according to claim 1.

13. A vector comprising an isolated nucleic acid molecule according to claim 12.

14. An isolated recombinant cell comprising an isolated nucleic acid molecule according to claim 12.

15. An isolated recombinant cell according to claim 14 which is a mammalian cell.

16. A method of producing an antibody molecule according to claim 1, the method comprising culturing a recombinant cell comprising an isolated nucleic acid encoding the antibody, under conditions for expression of the antibody molecule.

17. A method according to claim 16 further comprising isolating and/or purifying the antibody molecule following expression.

18. A pharmaceutical composition comprising an antibody molecule according to claim 1 and a pharmaceutically acceptable excipient.

19. A method of treating a cancer that expresses tenascin-C, comprising administering an antibody molecule according to claim 1 to an individual in need thereof, wherein said antibody molecule is conjugated to a cytotoxic agent, a cytokine or a therapeutic radioisotope.

20. A method according to claim 19 wherein the cancer is leukaemia or glioma.

21. A method according to claim 19 wherein the antibody molecule is administered in combination with a second therapeutic agent.

* * * * *

SEQUENCE LISTING

<160> NUMBER OF SEQ ID NOS: 13

<210> SEQ ID NO 1
<211> LENGTH: 116
<212> TYPE: PRT
<213> ORGANISM: Artificial Sequence
<220> FEATURE:

<223> OTHER INFORMATION: F16 VH Domain

<400> SEQUENCE: 1

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Ser
        115
```

<210> SEQ ID NO 2
<211> LENGTH: 109
<212> TYPE: PRT
<213> ORGANISM: Artificial Sequence
<220> FEATURE:
<223> OTHER INFORMATION: Generic F16 VL domain
<220> FEATURE:
<221> NAME/KEY: MISC_FEATURE
<222> LOCATION: (88)..(88)
<223> OTHER INFORMATION: Xaa at position 88 is any amino acid except Xaa at position 88 is not Asn when Xaa at position 90 is Ser or Thr
<220> FEATURE:
<221> NAME/KEY: MISC_FEATURE
<222> LOCATION: (90)..(90)
<223> OTHER INFORMATION: Xaa at position 90 is any amino acid except Xaa at position 90 is not Ser or Thr when Xaa at position 88 is Asn

<400> SEQUENCE: 2

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Xaa Ser Xaa Val Tyr Thr Met Pro Pro
                85                  90                  95

Val Val Phe Gly Gly Gly Thr Lys Leu Thr Val Leu Gly
            100                 105
```

<210> SEQ ID NO 3
<211> LENGTH: 109
<212> TYPE: PRT
<213> ORGANISM: Artificial Sequence
<220> FEATURE:
<223> OTHER INFORMATION: N88Q mutation F16 VL domain

<400> SEQUENCE: 3

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln Ser Val Tyr Thr Met Pro Pro
                85                  90                  95

Val Val Phe Gly Gly Gly Thr Lys Leu Thr Val Leu Gly
            100                 105
```

<210> SEQ ID NO 4
<211> LENGTH: 214
<212> TYPE: PRT
<213> ORGANISM: Artificial Sequence
<220> FEATURE:
<223> OTHER INFORMATION: WT F16 light chain

<400> SEQUENCE: 4

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Val Tyr Thr Met Pro Pro
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
                180                 185                 190

Tyr Ser Cys Gln Val Thr His Glu Gly Ser Thr Val Glu Lys Thr Val
            195                 200                 205

Ala Pro Thr Glu Cys Ser
        210
```

<210> SEQ ID NO 5
<211> LENGTH: 446
<212> TYPE: PRT
<213> ORGANISM: Artificial Sequence
<220> FEATURE:

<223> OTHER INFORMATION: F16 heavy chain

<400> SEQUENCE: 5

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Ser Asp Lys Thr His Thr
    210                 215                 220

Ser Pro Pro Ser Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 6
<211> LENGTH: 214
<212> TYPE: PRT
<213> ORGANISM: Artificial Sequence
<220> FEATURE:
<223> OTHER INFORMATION: N88Q F16 light chain

<400> SEQUENCE: 6

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln Ser Ser Val Tyr Thr Met Pro Pro
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
            180                 185                 190

Tyr Ser Cys Gln Val Thr His Glu Gly Ser Thr Val Glu Lys Thr Val
        195                 200                 205

Ala Pro Thr Glu Cys Ser
        210

<210> SEQ ID NO 7
<211> LENGTH: 109
<212> TYPE: PRT
<213> ORGANISM: Artificial Sequence
<220> FEATURE:
<223> OTHER INFORMATION: WT F16 VL domain

<400> SEQUENCE: 7

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45
```

Gly Lys Asn Asn Arg Pro Ser Gly Ile Pro Asp Arg Phe Ser Gly Ser
            50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Ser Val Tyr Thr Met Pro Pro
                 85                  90                  95

Val Val Phe Gly Gly Gly Thr Lys Leu Thr Val Leu Gly
            100                 105

<210> SEQ ID NO 8
<211> LENGTH: 45
<212> TYPE: DNA
<213> ORGANISM: Artificial Sequence
<220> FEATURE:
<223> OTHER INFORMATION: F16SpeILedSeqFo SDM primer

<400> SEQUENCE: 8
cagactagtg tcgaccatgg gctggagcct gatcctcctg ttcct                45

<210> SEQ ID NO 9
<211> LENGTH: 39
<212> TYPE: DNA
<213> ORGANISM: Artificial Sequence
<220> FEATURE:
<223> OTHER INFORMATION: F16LCNuuQRev SDM primer

<400> SEQUENCE: 9
catagtataa acagaggatt gacagtaata gtcagcctc                       39

<210> SEQ ID NO 10
<211> LENGTH: 39
<212> TYPE: DNA
<213> ORGANISM: Artificial Sequence
<220> FEATURE:
<223> OTHER INFORMATION: F16LCN88Q SDM primer

<400> SEQUENCE: 10
gaggctgact attactgtca atcctctgtt tatactatg                       39

<210> SEQ ID NO 11
<211> LENGTH: 45
<212> TYPE: DNA
<213> ORGANISM: Artificial Sequence
<220> FEATURE:
<223> OTHER INFORMATION: F16EcoRIRev SDM primer

<400> SEQUENCE: 11
caggaattct tactatgaac attctgtagg ggccactgtc ttctc                45

<210> SEQ ID NO 12
<211> LENGTH: 133
<212> TYPE: PRT
<213> ORGANISM: Homo sapiens IL-2 amino acid sequence

<400> SEQUENCE: 12

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys

-continued

```
                50                  55                  60
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 13
<211> LENGTH: 379
<212> TYPE: PRT
<213> ORGANISM: Artificial Sequence
<220> FEATURE:
<223> OTHER INFORMATION: F16-IL2 Immunocytokine amino acid sequence

<400> SEQUENCE: 13

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
                20                  25                  30

Gly Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
                100                 105                 110

Thr Val Ser Arg Gly Ser Ser Gly Gly Ser Ser Glu Leu Thr Gln Asp
            115                 120                 125

Pro Ala Val Ser Val Ala Leu Gly Gln Thr Val Arg Ile Thr Cys Gln
    130                 135                 140

Gly Asp Ser Leu Arg Ser Tyr Tyr Ala Ser Trp Tyr Gln Gln Lys Pro
145                 150                 155                 160

Gly Gln Ala Pro Val Leu Val Ile Tyr Gly Lys Asn Asn Arg Pro Ser
                165                 170                 175

Gly Ile Pro Asp Arg Phe Ser Gly Ser Ser Ser Gly Asn Thr Ala Ser
            180                 185                 190

Leu Thr Ile Thr Gly Ala Gln Ala Glu Asp Glu Ala Asp Tyr Tyr Cys
        195                 200                 205

Gln Ser Ser Val Tyr Thr Met Pro Pro Val Val Phe Gly Gly Gly Thr
    210                 215                 220

Lys Leu Thr Val Leu Glu Phe Ser Ser Ser Gly Ser Ser Ser Ser
225                 230                 235                 240

Gly Ser Ser Ser Gly Ala Pro Thr Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Phe
```

-continued

```
            275                 280                 285
Lys Phe Tyr Met Pro Lys Lys Ala Thr Glu Leu Lys His Leu Gln Cys
    290                 295                 300

Leu Glu Glu Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
                355                 360                 365

Thr Phe Cys Gln Ser Ile Ile Ser Thr Leu Thr
    370                 375
```